United States Patent
Tolan et al.

(10) Patent No.: US 11,312,977 B2
(45) Date of Patent: Apr. 26, 2022

(54) PRETREATMENT WITH LIGNOSULFONIC ACID

(71) Applicant: Iogen Corporation, Ottawa (CA)

(72) Inventors: Jeffrey S. Tolan, Ottawa (CA); Brian Foody, Ottawa (CA); Daniel G. MacDonald, Orleans (CA)

(73) Assignee: Iogen Corporation, Ottawa (CA)

(*) Notice: Subject to any disclaimer, the term of this patent is extended or adjusted under 35 U.S.C. 154(b) by 0 days.

(21) Appl. No.: 17/040,738

(22) PCT Filed: Nov. 9, 2018

(86) PCT No.: PCT/CA2018/000214
§ 371 (c)(1),
(2) Date: Sep. 23, 2020

(87) PCT Pub. No.: WO2019/191828
PCT Pub. Date: Oct. 10, 2019

(65) Prior Publication Data
US 2021/0010036 A1     Jan. 14, 2021

Related U.S. Application Data

(60) Provisional application No. 62/654,116, filed on Apr. 6, 2018.

(51) Int. Cl.
*C12P 7/10* (2006.01)
*C12P 19/02* (2006.01)

(52) U.S. Cl.
CPC ............... *C12P 7/10* (2013.01); *C12P 19/02* (2013.01); *C12P 2201/00* (2013.01); *C12P 2203/00* (2013.01)

(58) Field of Classification Search
None
See application file for complete search history.

(56) References Cited

U.S. PATENT DOCUMENTS

| | | | |
|---|---|---|---|
| 2,060,068 A | 11/1936 | Groombridge et al. |
| 2,418,167 A | 4/1947 | Du Bois |
| 2,710,254 A | 6/1955 | Van Blaricom et al. |

(Continued)

FOREIGN PATENT DOCUMENTS

| | | |
|---|---|---|
| EP | 0450430 B1 | 10/1991 |
| EP | 0715657 B1 | 6/1996 |

(Continued)

OTHER PUBLICATIONS

Auxenfans et al., "Understanding the structural and chemical changes of plant biomass following steam explosion pretreatment," Biotechnol. Biofuels, 2017, vol. 10, No. 36.

(Continued)

*Primary Examiner* — Richard C Ekstrom
(74) *Attorney, Agent, or Firm* — Knobbe Martens Olson & Bear LLP

(57) ABSTRACT

A process for converting lignocellulosic biomass to glucose or ethanol includes subjecting the lignocellulosic biomass to a lignosulfonic acid pretreatment, wherein the lignosulfonic acid has a concentration of sulfonate groups in acid form that is greater than 0.02 mol/L and a total amount of sulfur dioxide is greater than 15 wt % based on dry weight of lignocellulosic biomass.

20 Claims, 9 Drawing Sheets

(56) References Cited

U.S. PATENT DOCUMENTS

| | | |
|---|---|---|
| 2,710,255 A | 6/1955 | Van Blaricom et al. |
| 3,046,182 A | 11/1956 | Tomlinson et al. |
| 3,148,177 A | 9/1964 | Wiley et al. |
| 3,251,820 A | 5/1966 | Grangaard |
| 3,297,676 A | 1/1967 | Brauns |
| 4,295,929 A | 10/1981 | Leithem |
| 4,336,189 A | 6/1982 | Hamala et al. |
| 4,461,648 A | 7/1984 | Foody |
| 4,631,129 A | 12/1986 | Heikkila |
| 4,988,799 A * | 1/1991 | Samson ............... A61K 31/715 530/505 |
| 5,096,540 A | 3/1992 | Sell et al. |
| 5,424,417 A | 6/1995 | Torget et al. |
| 5,637,225 A | 6/1997 | Heikkila et al. |
| 5,777,086 A | 7/1998 | Klyosov et al. |
| 5,789,210 A | 8/1998 | Ho et al. |
| 5,866,382 A | 2/1999 | Hallborn et al. |
| 6,475,768 B1 | 11/2002 | Otero et al. |
| 6,582,944 B1 | 6/2003 | Hallborn et al. |
| 7,198,925 B2 | 4/2007 | Foody |
| 7,527,927 B1 | 5/2009 | Ho et al. |
| 7,527,951 B2 | 5/2009 | Londesborough et al. |
| 7,585,652 B2 | 9/2009 | Foody et al. |
| 7,622,284 B2 | 11/2009 | Op Den Camp et al. |
| 7,709,042 B2 | 5/2010 | Foody et al. |
| 7,754,456 B2 | 7/2010 | Penttila et al. |
| 7,754,457 B2 | 7/2010 | Foody et al. |
| 7,901,511 B2 | 3/2011 | Griffin et al. |
| 7,993,463 B2 | 8/2011 | Griffin et al. |
| 8,017,361 B2 | 9/2011 | Scott et al. |
| 8,017,820 B2 | 9/2011 | Foody et al. |
| 8,038,842 B2 | 10/2011 | Retsina et al. |
| 8,252,568 B2 | 8/2012 | Foody et al. |
| 8,268,125 B2 | 9/2012 | Retsina et al. |
| 8,328,947 B2 | 12/2012 | Anand et al. |
| 8,409,836 B2 | 4/2013 | Vehmaanpera et al. |
| 8,603,789 B2 | 12/2013 | Harlick |
| 8,709,770 B2 | 4/2014 | Harlick et al. |
| 8,728,243 B2 | 5/2014 | Van Der Meulen et al. |
| 8,815,499 B2 | 8/2014 | Alriksson et al. |
| 8,815,561 B2 | 8/2014 | Liu et al. |
| 8,834,633 B2 | 9/2014 | Van Der Meulen et al. |
| 8,835,156 B2 | 9/2014 | Bjornsson et al. |
| 8,853,478 B2 | 10/2014 | Machhammer et al. |
| 8,871,475 B2 | 10/2014 | Alriksson et al. |
| 8,993,274 B2 | 3/2015 | Romero |
| 9,012,188 B2 | 4/2015 | Van Heiningen et al. |
| 9,068,236 B2 | 6/2015 | Heikkila et al. |
| 9,074,231 B2 | 7/2015 | Zhu |
| 9,090,915 B2 | 7/2015 | Wang et al. |
| 9,102,951 B2 | 8/2015 | Griffin et al. |
| 9,212,401 B2 | 12/2015 | Weider et al. |
| 9,243,364 B2 | 1/2016 | Zhu et al. |
| 9,284,382 B2 | 3/2016 | Chen et al. |
| 9,290,821 B2 | 3/2016 | Blackbourn et al. |
| 9,303,253 B2 | 4/2016 | Van Maris et al. |
| 9,399,840 B2 | 7/2016 | Nelson et al. |
| 9,434,961 B2 | 9/2016 | Dottori et al. |
| 9,624,436 B2 | 1/2017 | Hamilton et al. |
| 9,574,212 B2 | 2/2017 | Foody et al. |
| 9,631,316 B2 | 4/2017 | Retsina et al. |
| 9,738,729 B2 | 8/2017 | Retsina et al. |
| 9,783,565 B2 | 10/2017 | Carlius et al. |
| 9,856,605 B2 | 1/2018 | Retsina |
| 9,873,665 B2 | 1/2018 | Blackbourn et al. |
| 10,144,939 B2 | 12/2018 | Noodam et al. |
| 10,316,336 B2 | 6/2019 | Survase et al. |
| 10,421,667 B2 | 9/2019 | Foody et al. |
| 10,513,714 B2 | 12/2019 | Foody et al. |
| 10,513,715 B2 | 12/2019 | Foody et al. |
| 10,655,149 B2 | 5/2020 | Dechman et al. |
| 10,662,455 B2 | 5/2020 | Tolan et al. |
| 10,995,314 B2 | 5/2021 | Foody et al. |
| 11,008,598 B2 | 5/2021 | Foody et al. |
| 2007/0254348 A1 | 9/2007 | Retsina et al. |
| 2009/0118477 A1 | 5/2009 | Hallberg et al. |
| 2010/0056774 A1 | 3/2010 | Anand et al. |
| 2010/0279361 A1 | 11/2010 | South et al. |
| 2011/0165643 A1 | 7/2011 | Retsina et al. |
| 2011/0207922 A1 | 8/2011 | Kubo et al. |
| 2011/0250638 A1 | 10/2011 | Sjoede et al. |
| 2011/0300586 A1 | 12/2011 | Liu et al. |
| 2012/0041186 A1 | 2/2012 | Pschorn et al. |
| 2012/0073199 A1 | 3/2012 | Lewis |
| 2012/0315674 A1 | 12/2012 | Realff et al. |
| 2013/0071903 A1 | 3/2013 | Rowland et al. |
| 2013/0118483 A1 | 5/2013 | Gao et al. |
| 2014/0024093 A1 | 1/2014 | Blackbourn et al. |
| 2014/0034047 A1 | 2/2014 | Retsina et al. |
| 2014/0053827 A1 | 2/2014 | Macedo Baudel et al. |
| 2014/0142351 A1 | 5/2014 | Johnston et al. |
| 2014/0154746 A1 | 6/2014 | Jonsson et al. |
| 2014/0163210 A1 | 6/2014 | Retsina et al. |
| 2014/0178944 A1 | 6/2014 | Parekh et al. |
| 2014/0182582 A1 | 7/2014 | Retsina et al. |
| 2014/0186899 A1 | 7/2014 | Retsina et al. |
| 2014/0186901 A1 | 7/2014 | Retsina et al. |
| 2014/0186903 A1 | 7/2014 | Retsina et al. |
| 2015/0047629 A1 | 2/2015 | Borden et al. |
| 2015/0225756 A1 | 8/2015 | Retsina et al. |
| 2015/0259709 A1 | 9/2015 | Retsina et al. |
| 2015/0299738 A1 | 10/2015 | Wang et al. |
| 2015/0299739 A1 | 10/2015 | Harlick et al. |
| 2016/0152779 A1 | 6/2016 | Pylkkanen et al. |
| 2016/0237102 A1 | 8/2016 | Retsina et al. |
| 2016/0237173 A1 | 8/2016 | Nelson et al. |
| 2016/0257979 A1 * | 9/2016 | Retsina ................... C12P 19/02 |
| 2016/0281298 A1 | 9/2016 | Nelson et al. |
| 2017/0002387 A1 | 1/2017 | Retsina et al. |
| 2017/0211231 A1 | 7/2017 | Baker et al. |
| 2018/0016607 A1 | 1/2018 | Hagglund |
| 2018/0037862 A1 | 2/2018 | Foody et al. |
| 2018/0037863 A1 | 2/2018 | Foody et al. |
| 2018/0037915 A1 | 2/2018 | Foody et al. |
| 2019/0127275 A1 | 5/2019 | Andresen et al. |
| 2019/0271114 A1 | 9/2019 | Nelson et al. |
| 2021/0010036 A1 * | 1/2021 | Tolan ................. D21C 11/0007 |

FOREIGN PATENT DOCUMENTS

| | | |
|---|---|---|
| WO | WO 89/08165 | 9/1989 |
| WO | WO2010/078930 | 7/2010 |
| WO | WO 2013/113579 A1 | 8/2013 |
| WO | WO 2015/103197 | 7/2015 |
| WO | WO 2016/113221 | 7/2016 |
| WO | WO 2017/112471 A1 | 6/2017 |
| WO | WO 2019/204190 | 10/2019 |
| WO | WO 2020/093131 | 5/2020 |
| WO | WO 2020/223792 | 11/2020 |

OTHER PUBLICATIONS

Balan, V., "Current Challenges in Commercially Producing Biofuels from Lignocellulosic Biomass" ISRN Biotechnology, 2014, Article No. 463074.

Behera et al., "Importance of chemical pretreatment for bioconversion of lignocellulosic biomass" 2014, Renewable and Sustainable Energy Reviews, pp. 91-106, vol. 36.

Benjamin et al., "A General Description of Commercial Wood Pulping and Bleaching Processes", Journal of the Air Pollution Control Association, 1969, pp. 155-161vol. 19, No. 3.

Bensah, E. and Mensah, M., "Chemical Pretreatment Methods for the Production of Cellulosic Ethanol: Technologies and Innovations," International Journal of Chemical Engineering, 2013, pp. 1-21, vol. 2013.

Bhalla et al., "Improved lignocellulose conversion to biofuels with thermophilic bacteria and thermostable enzymes," Bioresource Technology, 2013, pp. 751-759, vol. 128.

Boussaid et al., "Fermentability of the Hemicellulose-Derived Sugars from Steam-Exploded Softwood (Douglas Fir)," Biotechnology and Bioengineering, 1999, pp. 284-289, vol. 64, No. 3.

(56) References Cited

OTHER PUBLICATIONS

Brownell, H. and Saddler, J., "Steam Pretreatment of Lignocellulosic Material for Enhanced Enzymatic Hydrolysis," Biotechnology and Bioengineering, 1987, pp. 228-235, vol. 29.
Bruijnincx et al., "Lignin Valorisation the Importance of a Full Value Chain Approach," APC, 2016.
Bu et al., "Comparative Study of Sulfite Pretreatments for Robust Enzymatic Saccharification of Corn Cob Residue," Biotechnology for Biofuels, 2012, vol. 5, No. 87.
Bura et al., "Influence of Xylan on the Enzymatic Hydrolysis of Steam-Pretreated Corn Stover and Hybrid Poplar," Biotechnol Prog, 2009, pp. 315-322, vol. 25, No. 2.
Bura et al., "Moving towards commercialization of lignocellulosic biomass to fuels to chemicals. How to deal with heterogeneous biomass?" University of Washington Biofuels and Bioproducts Laboratory, 2012.
Bura et al., "Optimization of SO2-Catalyzed Steam Pretreatment of Corn Fiber for Ethanol Production", Applied Biochemistry and Biotechnology, 2003, vol. 105-108, pp. 319-335.
Bura et al., "SO2-Catalyzed Steam Explosion of Corn Fiber for Ethanol Production," Applied Biochemistry and Biotechnology, 2002, pp. 59-72, vols. 98-100.
Carrasco et al., "SO2-catalysed steam pretreatment of quinoa stalks," J Chem Technol Biotechnol, 2015, pp. 64-71, vol. 90.
Carrasco et al., "SO2-catalyzed steam pretreatment and fermentation of enzymatically hydrolyzed sugarcane bagasse," Enzyme and Microbial Technology, 2010, pp. 64-73, vol. 46.
Carrasco, "Arabinosylated phenolics obtained from SO2-steam-pretreated sugarcane bagasse," Journal of Chemical Technology and Biotechnology, 2012, pp. 1723-1726, vol. 87.
Chacha et al., "Steam Pretreatment of Pine (*Pinus patula*) Wood Residue for the Production of Reducing Sugars," Cellulose Chemistry and Technology, 2011, pp. 495-501, vol. 45 (7-8).
Chandra et al., "Enhancing Hemicellulose Recovery and the Enzymatic Hydrolysis of Cellulose by Adding Lignosulfonates during the Two-Stage Steam Pretreatment of Poplar," ACS Sustainable Chem Eng, 2015, pp. 986-991, vol. 3.
Cheng et al., "High titer and yield ethanol production from undetoxified whole slurry of Douglas-fir forest residue using pH profiling in SPORL," Biotechnology for Biofuels, 2015, pp. 1-10, vol. 8:22.
Chum et al., "Pretreatment—Catalyst Effects and the Combined Severity Parameter," Appl. Biochem. and Biotech., 1990, vol. 24/25.
Chylenski et al., "Enzymatic degradation of sulfite-pulped softwoods and the role of LPMOs," Biotechnol. Biofuels, 2017, 10/177.
Clark et al., "Steam Explosion of the Softwood Pinus Radiata with Sulphur Dioxide Addition. II. Process Characterisation," Journal of Wood Chemistry and Technology, 1989, pp. 135-166, vol. 9:2.
Clark et al., "Steam Explosion of the Softwood Pinus Radiata with Sulphur Dioxide Addition. I. Process Optimization," Journal of Wood Chemistry and Technology, 1987, pp. 373-403, vol. 7:3.
Corrales et al., "Structural evaluation of sugar cane bagasse steam pretreated in the presence of CO2 and SO2," Biotechnology for Biofuels, 2012, pp. 1-8, vol. 5:36.
De Bari et al., "SO2-Catalyzed Steam Fractionation of Aspen Chips for Bioethanol Production: Optimization of the Catalyst Impregnation," Ind. Eng. Chem. Res, 2007, pp. 7711-7720, vol. 46.
Dekker, R.F.H. et al., "Enzymic Saccharification of Sugarcane Bagasse Pretreated by Autohydrolysis-Steam Explosion," Biotechnology and Bioengineering, 1983, pp. 3027-3048, vol. XXV.
Dekker, Robert F. H., "The Utilization of Autohydrolysis-Exploded Hardwood (*Eucalyptus regnans*) and Softwood (*Pinus radiata*) Sawdust for the Production of Cellulolytic Enzymes and Fermentable Substrates," Biocatalysis, 1987, pp. 63-75, vol. 1.
Deshpande et al., "The reactivity of lignin carbohydrate complex (LCC) during manufacture of dissolving pulp from softwood," Industrial Crops & Products, 2018, pp. 315-322, vol. 115.
Deshpande, R., "The initial phase of sodium sulfite pulping of softwood", Doctoral Thesis, Karlstad University Studies, 2016.

Ehsanipour, Mandana, "Bioconversion of lignocellulosic hydrolysate to acetic acid using Moorella thermoacetica," a thesis submitted in partial fulfillment of the requirements for the degree of Master of Science at University of Washington, 2015.
Eklund et al., "The Influence of SO2 and H2SO4 Impregnation of Willow Prior to Steam Pretreatment," 1995, Bioresource Engineering, pp. 225-229, vol. 52.
Elander et al., "Summary of findings from the Biomass Refining Consortium for Applied Fundamentals and Innovation (CAFI): corn stover pretreatment," 2009, Cellulose, pp. 649-659, vol. 16.
Ewanick et al., "The effect of biomass moisture content on bioethanol yields from steam pretreated switchgrass and sugarcane bagasse," 2011, Bioresource Technology, pp. 2651-2658, vol. 102.
Fan et al., "Optimization of SO2-catalyzed hydrolysis of corncob for xylose and xylitol production," 2014, J Chem Technol Biotechnol, pp. 1720-1726, vol. 89.
Fatehi et al., "Extraction of Technical Lignins from Pulping Spent Liquors, Challenges and Opportunities," Chapter 2 Production of Biofuels and Chemicals from Lignin, 2016, pp. 35-54.
Felby et al., "Ethanol from Wheat Straw Cellulose by Wet Oxidation Pretreatment and Simultaneous Saccharification and Fermentation", American Chemical Society, ACS Symposium Series, 2003, pp. 157-174.
Frolander, et al., "Conversion of cellulose, hemicellulose and lignin into platform molecules: biotechnological approach," Eurobioref. 2011.
Galbe et al., "A review of the production of ethanol from softwood," 2002, Appl Microbial Biotechnol, pp. 618-628, vol. 59.
Gao et al., "Lignin triggers irreversible cellulase loss during pretreated lignocellulosic biomass saccharification," Biotechnology for Biofuels, 2014, vol. 14, No. 175.
Gao et al., "Saccharification of recalcitrant biomass and integration options for lignocellulosic sugars from Catchlight Energy's sugar process (CLE Sugar)," Biotechnology for Biofuels, 2013, vol. 6, No. 10.
Garlock et al., "Comparative material balances around pretreatment technologies for the conversion of switchgrass to soluble sugars," 2011, Bioresource Technology, pp. 11063-11071, vol. 102.
Gelosia et al., "Fractionation of Lignocellulosic Residues Coupling Steam Explosion and Organosolv Treatments Using Green Solvent Valerolactone," Energies, 2017, vol. 10.
Gregg et al., "A Techno-Economic Assessment of the Pretreatment and Fractionism Steps of a Biomass-to-Ethanol Process," 1996, Applied Biochemistry and Biotechnology, pp. 711-727, vol. 57/58.
Gu et al., "Fermentative High-Titer Ethanol Production from Douglas-Fir Forest Residue Without Detoxification Using SPORL: High SO2 Loading at Low Temperature," 2016, Industrial Biotechnology, pp. 168-175, vol. 12, No. 3.
Harris et al., "Stimulation of Lignocellulosic Biomass Hydrolysis by Proteins of Glycoside Hydrolase Family 61: Structure and Function of a Large, Enigmatic Family," 2010, Biochemistry, pp. 3305-3316, vol. 49.
Hodge et al., "Soluble and insoluble solids contributions to high-solids enzymatic hydrolysis of lignocellulose," 2008, Bioresource Technology, pp. 8940-8948, vol. 99.
Huang et al., "Novel process for the coproduction of xylo-oligosaccharides, fermentable sugars, and lignosulfonates from hardwood," Bioresource Technology, 2016, pp. 600-607, vol. 219.
Iakovlev et al., "Kinetics of fractionation by SO2-ethanol-water (SEW) treatment: understanding the deconstruction of spruce wood chips," RSC Advances, 2012, pp. 3057-3068, vol. 2, No. 7.
Iakovlev et al., "SO2-ethanol-water (SEW) fractionation process: Production of dissolving pulp from spruce," Cellulose, 2014, pp. 1419-1429, vol. 21.
Karimi et al., "A critical review of analytical methods in pretreatment of lignocelluloses: Composition, imaging, and crystallinity," Bioresource Technology, 2016, pp. 1008-1018, vol. 200.
Keller et al., "Magnesium Bisulfite Pulping and Papermaking with Southern Pine," US Forest Service Research Paper, 1967.
Kilian, A., "Control of an acid sulphite batch pulp digester based on a fundamental process model,", Master Thesis, 1999, University of Pretoria.

(56) References Cited

OTHER PUBLICATIONS

Kumar et al., "Access of Cellulase to Cellulose and Lignin for Poplar Solids Produced by Leading Pretreatment Technologies," 2009, Biotechnol. Prog., pp. 807-819, vol. 25, No. 3.
Kumar et al., "Effects of Cellulase and Xylanase Enzymes on the Deconstruction of Solids from Pretreatment of Poplar by Leading Technologies," Biotechnol. Prog., 2009, pp. 302-314, vol. 25, No. 2.
Kumar et al., "Recent updates on different methods of pretreatment of lignocellulosic feedstocks: a review," Bioresour Bioprocess, 2017, vol. 4., No. 7.
Lan et al., "High titer ethanol production from SPORL-pretreated lodgepole pine by simultaneous enzymatic saccharification and combined fermentation," 2013, Bioresource Technology, pp. 291-297, vol. 127.
Leu et al., "Substrate-Related Factors Affecting Enzymatic Saccharification of Lignocelluloses; Our Recent Understanding," 2013, Bioenerg. Res., pp. 405-415, vol. 6.
Liu et al., "Multistep Process to Produce Fermentable Sugars and Lignosulfonates from Softwood Enzymolysis Residues," ACS Sustainable Chem. Eng., 2016, pp. 7225-7230, vol. 4.
Liu et al., "Effect of Sulfite Pretreatment to Overcome the Recalcitrance of Lignin (SPORL) on Enzymatic Saccharification of Corn Stalk," 2011, Bioresouces, 5001-5011, vol. 6(4).
Llano et al., "Detoxification of a Lignocellulosic Waste from a Pulp Mill to Enhance Its Fermentation Prospects", Energies, 2017, vol. 10, No. 348.
Mackie et al., "Effect of Sulphur Dioxide and Sulphuric Acid on Steam Explosion of Aspenwood," 1985, Journal of Wood Chemistry and Technology, pp. 405-425, vol. 5(3).
Mamers et al., "Explosion pretreatment of Pinus radiata woodchips for the production of fermentation substrates," 1984, Apita, pp. 644-649, vol. 37, No. 8.
Martin et al., "Comparison of the Fermentability of Enzymatic Hydrolyzates of Sugarcane Bagasse Pretreated by Steam Explosion Using Different Impregnating Agents," 2002, Applied Biochemistry and Biotechnology, pp. 699-716, vol. 98-100.
Miles-Barrett et al., "Use of Bisulfite Processing to Generate Hight BO4 Content Water Soluble Lignosulfonates," ACS Sustainable Chem. Eng., 2017, pp. 1831-1839, vol. 5.
Monavari et al., "Improved One-Step Steam Pretreatment if SO2-Impregnated Softwood with Time-Dependant Temperature Profile for Ethanol Production," 2010, Biotechnol. Prog., pp. 1054-1060, vol. 26.
Mupondwa et al., "Status of Canada's lignocellulosic ethanol: Part I: Pretreatment technologies," Renewable and Sustainable Energy Reviews, 2017, pp. 178-190, vol. 72.
Nguyen et al., "Dilute Acid Pretreatment of Softwoods," 1998, Applied Biochemistry and Biotechnology, pp. 77-89, vol. 70-72.
Nguyen et al., "Two-Stage Dilute Acid Pretreatment of Softwoods," 2000, Applied Biochemistry and Biotechnology, 561-576, vol. 84-86.
Nrel, "Continual Shrinking-Bed Reactor Boosts Biomass Ethanol," Research Brief, (2020).
Ohgren et al., "Optimization of Steam Pretreatment of SO2-Impregnated Corn Stover for Fuel Ethanol Production," 2005, Applied Biochemistry and Biotechnology, pp. 1055-1067, vol. 121-124.
Pan et al., "Woody Biomass Sulfite Pretreatment to Overcome Lignocellulose Recalcitrance for Biofuel Production", Wisconsin Alumni Research Foundation, (2020).
Paulova et al., "Production of $2^{nd}$ Generation of Liquid Biofuels", Liquid Gaseous and Solid Biofuels—Conversion Techniques, 2013.
Pedersen et al., "Low temperature lignocellulose pretreatment: effects and interactions of pretreatment pH are critical for maximizing enzymatic monosaccharide yields from wheat straw," 2011, Biotechnology for Biofuels, pp. 1-10, vol. 4:11.
Rakkolainen et al., "SO2-Ethanol-Water Fractionation of Forest Biomass and Implications for Biofuel Production by Abe Fermentation," 2010, Cellulose Chem. Technol., pp. 139-145, vol. 44.
Ramos et al., "Characterization of Residual Lignin after SO2-Catalyzed Steam Explosion and Enzymatic Hydrolysis of Eucalyptus viminalis Wood Chips," 1999, J. Agric. Food Chem., pp. 2295-2302, vol. 47.
Ramos et al., "Comparison of Steam Pretreatment of Eucalyptus, Aspen, and Spruce Wood Chips and their Enzymatic Hydrolysis," 1992, Applied Biochemistry and Biotechnology, pp. 37-48, vol. 34/35.
Ramos et al., "Effect of enzymatic hydrolysis on the morphology and fine structure of pretreated cellulosic residues," 1993, Enzyme Microb. Technol., pp. 821-831, vol. 15.
Reknes, K., "The chemistry of lignosulphonate and the effect on performance of lignosulfonate base plasticizers and superplasticizers," $29^{th}$ Conference on Our World in Concrete & Structures, Aug. 2004, Singapore.
Rodsrud et al., "History and future of world's most advanced biorefinery in operation", Biomass and Bioenergy, 2012, vol. 46, pp. 46-59.
Rollin et al., "Increasing Cellulose Accessibility is More Important than Removing Lignin: A Comparison of Cellulose Solvent-Based Lignocellulose Fractionation and Soaking in Aqueous Ammonia," Biotechnology and Bioengineering, 2011, pp. 22-30, vol. 108. No. 1.
Sassner et al., "Steam Pretreatment of Salix with and without SO2 Impregnation for Production of Bioethanol," 2005, Applied Biochemistry and Biotechnology, pp. 1101-1117, vol. 121-124.
Schell et al., "A Technical and Economic Analysis of Acid-Catalyzed Steam Explosion and Dilute Sulfuric Acid Pretreatments Using Wheat Straw or Aspen Wood Chips," 1991, Applied Biochemistry and Biotechnology, pp. 87-97, vol. 28/29.
Schell et al., "Pretreatment of Softwood by Acid-Catalyzed Steam Explosion Followed by Alkali Extraction," 1998, Applied Biochemistry and Biotechnology, pp. 17-24, vol. 70-72.
Schwald et al., "Assessment of Pretreatment Conditions to Obtain Fast Complete Hydrolysis on High Substrate Concentrations," 1989, Applied Biochemistry and Biotechnology, pp. 29-44, vol. 20/21.
Selig et al., "The Effect of Lignin Removal by Alkaline Peroxide Pretreatment on the Susceptibility of Corn Stover to Purified Celluloytic and Xylanolytic Enzymes," Appl. Biochem. Biotechnol., 2009, pp. 397-406, Vo. 155.
Sendelius, "Steam Pretreatment Optimisation for Sugarcane Bagasse in Bioethanol Production," 2005, Master of Science Thesis, Lund University, Sweden.
Shahzad, M. A., "Effect of temperature and time on acid sulfite cooking for dissolving pulp," Degree Project, Karlstad University, 2012.
Shevchenko et al., "Optimization of monosaccharide recovery by post-hydrolysis of the water-soluble hemicellulose component after steam explosion of softwood chips," 2000, Bioresource Technology, pp. 207-211, vol. 72.
Shevchenko et al., "The Nature of Lignin from Steam Explosion/Enzymatic Hydrolysis of Softwood," 1999, Applied Biochemistry and Biotechnology, pp. 867-876, vol. 77-79.
Shi et al., "Sugar yields from dilute sulfuric acid and sulfur dioxide pretreatments and subsequent enzymatic hydrolysis of switchgrass," 2011, Bioresource Technology, pp. 8930-8938, vol. 102.
Shi et al., "Pretreatment of Lignocellulosic Biomass", Beems Module B1, (2009).
Shuai et al., "Comparative study of SPORL and dilute-acid pretreatments of spruce for cellulosic ethanol production," 2010, Bioresource Technology, pp. 3106-3114, vol. 101.
Sipos et al., "Steam pretreatment of dry and ensiled industrial hemp for ethanol production," 2010, Biomass and Bioenergy, pp. 1-11.
Sixta, H., "Conventional Acid Sulfite Pulping," Aalto University, 2015.
Sluiter et al., "Determination of Structural Carbohydrates and Lignin in Biomass," NREL Technical Report 2012.
Soderstrom et al., "Effect of Washing on Yield in One- and Two-Step Steam Pretreatment of Softwood for Production of Ethanol," 2004, Biotechnol. Prog., pp. 744-749, vol. 20.

(56) References Cited

OTHER PUBLICATIONS

Soderstrom et al., "Separate versus Simultaneous Saccharification and Fermentation of Two-Step Steam Pretreated Softwood for Ethanol Production," 2005, Journal of Wood Chemistry, pp. 187-202, vol. 25.

Soderstrom et al., "Two-Step Steam Pretreatment of Softwood with SO2 Impregnation for Ethanol Production," 2002, Applied Biochemistry and Biotechnology, pp. 5-21, vol. 98-100.

Stenberg et al, "Optimisation of Steam Pretreatment of SO2-Impregnated Mixed Softwoods for Ethanol Production," 1998, J. Chem. Technol. Biotechnol, pp. 299-308, vol. 71.

Sumerskii et al., "Fast track for quantitative isolation of lignosulfonates from spent sulfite liquors," RSC Advances, 2015, pp. 92732-92742, vol. 5.

Szengyel et al., "Cellulase Production of Trichoderma reesei Rut C 30 Using Steam-Pretreated Spruce," 2000, Applied Biochemistry and Biotechnology, pp. 679-691, vol. 84-86.

Tao et al., "Process and technoeconomic analysis of leading pretreatment technologies for lignocellulosic ethanol production using switchgrass," 2011, Bioresource Technology, pp. 11105-11114, vol. 102.

Tengborg et al., "Comparison of SO2 and H2SO4 Impregnation of Softwood Prior to Steam Pretreatment on Ethanol Production," 1998, Applied Biochemistry and Biotechnology, pp. 3-15, vol. 70-72.

Tengborg et al., "Reduced inhibition of enzymatic hydrolysis of steam-pretreated softwood," 2001, Enzyme and Microbial Technology, pp. 835-844, vol. 28.

Thompson et al., "Chemical preconversion: application of low-severity pretreatment chemistries for commoditization of lignocellulosic feedstock," Biofuels, 2013, pp. 323-340, vol. 4, No. 3.

Tian et al., "Comparisons of SPORL and Dilute Acid Pretreatments for Sugar and Ethanol Productions from Aspen," 2011, Biotechnol. Prog. pp. 419-427, vol. 27, No. 2.

Tian et al., "Robust cellulosic ethanol production from SPORL-pretreated lodgepole pine using an adapted strain *Saccharomyces cerevisiae* without detoxification," 2010, Bioresource Technology, pp. 8678-8685, vol. 101.

Tian et al., "A comparison of various lignin-extraction methods to enhance the accessibility and ease of enzymatic hydrolysis of the cellulosic component of steam-pretreated poplar," Biotechnol. Biofuels, 2017, vol. 10, No. 157.

Trajano et al., "Fundamentals of Biomass Pretreatment at Low pH," 2013, Aqueous Pretreatment of Plant Biomass for Biological and Chemical Conversion to Fuels and Chemicals, pp. 103-128.

Vera et al., "Synergistic effects of mixing hybrid poplar and wheat straw biomass for bioconversion processes," 2015, Biotechnol Biofuels, pp. 1-10, vol. 8:226.

Vermaas et al., "Mechanism of lignin inhibition of enzymatic biomass deconstruction," Biotechnol Biofuels, 2015, vol. 8, No. 217.

Von Sivers et al., "A Techno-Economical Comparison of Three Processes for the Production of Ethanol from Pine," 1995, Bioresource Technology, pp. 43-52, vol. 51.

Wang et al., "Ethanol production from poplar wood through enzymatic saccharification and fermentation by dilute acid and SPORL pretreatments," 2012, Fuel, pp. 606-614, vol. 95.

Wang et al., "Influence of lignin addition on the enzymatic digestibility of pretreated lignocellulosic biomasses," Bioresource Technology, 2015, pp. 7-12, vol. 181.

Wang et al., "Lignosulfonate and elevated pH can enhance enzymatic saccharification of lignocelluloses," 2013, Biotechnology for Biofuels, pp. 1-10, vol. 6:9.

Wang et al., "Sulfite Pretreatment to Overcome Recalcitrance of Lignocellulose (SPORL) for Robust Enzymatic Saccharification of Hardwoods," 2009, Biotechnol. Prog., pp. 1086-1093, vol. 25, No. 4.

Wayman et al., "Hydrolysis of Biomass by Sulphur Dioxide," 1984, Biomass, pp. 183-191, vol. 6.

Wayman et al., "SO2 Catalysed Prehydrolysis of Coniferous Wood for Ethanol Production," 1986, Biotechnology Letters, pp. 749-752, vol. 8, No. 10.

Wiman et al., "Cellulose accessibility determines the rate of enzymatic hydrolysis of steam-pretreated spruce," 2012, Bioresource Technology, pp. 208-215, vol. 126.

Wolfinger et al., "Modeling of the Acid Sulfite Pulping Process.— Problem Definition and Theoretical Approach for a Solution with the Main Focus on the Recovery of Cooking Chemicals," 2004, Lenzinger Berichte, pp. 35-45, vol. 83.

Wooley, Bob, "Production of 1,000 Gallons of BioJet," 2015, Presentation from 2015 Annual Meeting of Northwest Advanced Renewables Alliance (NARA).

Wyman et al., "Comparative data on effects of leading pretreatments and enzyme loadings and formulations on sugar yields from different switchgrass sources," 2011, Bioresource Technology, 11052-11062.

Wyman et al., "Comparative Sugar Recovery and Fermentation Data Following Pretreatment of Poplar Wood by Leading Technologies," 2009, Biotechnol. Prog., pp. 333-339, vol. 25, No. 2.

You et al., "Kinetics of SO2-ethanol-water (AVAP) fractionation of sugarcane straw," Bioresource Technology, 2016, pp. 111-119, vol. 210.

Zhang et al., "Sulfite (SPORL) pretreatment of switchgrass for enzymatic saccharification," 2013, Bioresource Technology, pp. 127-134, vol. 129.

Zhou et al., "Bioconversion of Beetle-Killed Lodgepole Pine Using SPORL: Process Scale-Up Design, Lignin Coproduct, and High Solids Fermentation without Detoxification," 2013, Industrial & Engineering Chemistry Research, pp. A-I.

Zhou et al., "Comparisons of high titer ethanol production and lignosulfonate properties by SPORL pretreatment of lodgepole pine at two temperatures," RSC Advances, 2014, pp. 27030-27038, vol. 4.

Zhou et al., "High titer ethanol and lignosulfonate production from SPORL pretreated poplar at pilot scale," Frontier in Energy Research, 2015, vol. 3.

Zhu et al., "Case studies on sugar production from underutilized woody biomass using sulfite chemistry", Tappi Journal, 2015, pp. 577-583, vol. 14, No. 9.

Zhu et al., "Ethanol production from SPORL-pretreated lodgepole pine: preliminary evaluation of mass balance and process energy efficiency," 2010, Appl Microbiol Biotechnol, pp. 1355-1365, vol. 86.

Zhu et al., "High Titer Ethanol Production from Forest Residue Using Sulfite Mill Pulping Chemistry," 2015, Presentation at 2015 TAPPI IBBC.

Zhu et al., "High titer ethanol production from simultaneous enzymatic saccharification and fermentation of aspen at high solids: A comparison between SPORL and dilute acid pretreatments," 2011, Bioresource Technology, pp. 8921-8929, vol. 102.

Zhu et al., "On Polydispersity of Plant Biomass Recalcitrance and Its Effects on Pretreatment Optimization for Sugar Production," 2011, Bioenerg. Res., pp. 201-210, vol. 4.

Zhu et al., "Quantitative predictions of bioconversion of aspen by dilute acid and SPORL pretreatments using a unified combined hydrolysis factor (CHF)," 2012, Process Biochemistry, pp. 785-791, vol. 47.

Zhu et al., "Sulfite pretreatment (SPORL) for robust enzymatic saccharification of spruce and red pine," 2009, Bioresource Technology, pp. 2411-2418, vol. 100.

Zhu et al., "Using sulfite chemistry for robust bioconversion of Douglas-fir forest residue to bioethanol at high titer and lignosulfonate: A pilot-scale evaluation," 2015, Bioresource Technology, pp. 390-397, vol. 179.

Zhu et al., "Woody biomass pretreatment for cellulosic ethanol production: Technology and energy consumption evaluation," 2010, Bioresource Technology, pp. 4992-5002, vol. 101.

International Search Report and Written Opinion dated Apr. 5, 2019 for PCT Application No. PCT/CA2018/000214, filed Nov. 9, 2018.

Zhu et al., "Applications of lignin-derived catalysts for green synthesis", Green Energy & Environment, https://doi.org/10.1016/j.gee.2019.01.003.

(56) References Cited

OTHER PUBLICATIONS

Deshpande et al., "The Influence of Different Types of Bisulfite Cooking Liquors on Pine Wood Components," BioResources 11(3), 5961-5973, (2016).
Ren et al., "Comparative Evaluation of Magnesium Bisulfite Pretreatment under Different pH Values for Enzymatic Hydrolysis of Corn Stover," BioResources 11(3), 7258-7270, (2016).
Shi et al., "Degradation Kinetics of Monosaccharides in Hydrochloric Sulfuric and Sulfurous Acid," BioResources, 7(3), 4085-4097, (2012).
Takahashi, S. et al., "Removal of Acetic Acid From Sent Sulfite Liquor Using Anion Exchange Resin for Effective Xylose Fermentation with Pichia stiptis," BioResources, 8(2), 2417-2428, (2013).
Office Action issued in U.S. Appl. No. 16/761,180 dated Jun. 24, 2021.
Office action issued in U.S. Appl. No. 16/761,192 dated Sep. 2, 2021.
Andritz, "BioFuel Equipment—derived from Pulp and Fiberboard applications for Ligno-Cellulosic BioFuel & BioChemicals Technology" 2012.
Gellerstedt et al. "Towards a new concept of lignin condensation in Kraft pulping" C.R. Biologies, 2004, vol. 327.
Gratzel J et al. "Chemistry of Pulping: lignin reactions." American Chemical Society Symposium Series, 2000, vol. Ch. 20, pp. p 3932-421.
McElroy "Not so run of the Mill", Biomassmagazine, 2018 http://biomassmagazine.com/articles/1297/not-so-run-of-the-mill.
Philips, et al., "Integration of pulp and paper technology with bioethanol production", Biotechnology for Biofuels 2013 6:13.
Yan M., et al. "Influence of pH on the behaviour of lignosulfonate macromolecules in aqueous solution". Colloids and Surfaces: A Physiochemical and Engineering aspects, Nov. 1, 2010 (Jan. 11, 2010), vol. 37(1) pp. p. 50-58.

* cited by examiner

PRETREATMENT WITH LIGNOSULFONIC ACID

CROSS-REFERENCE TO RELATED APPLICATIONS

This application claims the priority benefit of provisional application No. 62/654,116, filed Apr. 6, 2018, which is incorporated herein by reference.

TECHNICAL FIELD

The present disclosure relates generally to a process and/or system for converting lignocellulosic biomass to glucose or a fermentation product, where the lignocellulosic biomass is pretreated with lignosulfonic acid prior to enzymatic hydrolysis.

BACKGROUND

Lignocellulosic biomass is an abundant material that contains lignocellulose (i.e., a complex of lignin and cellulose present in the cell walls of woody plants). Lignocellulosic biomass can be used to produce biofuels (e.g., ethanol, butanol, methane) by breaking down the cellulose and/or hemicellulose found in lignocellulosic biomass into their corresponding monomers (e.g., sugars). For example, cellulose may be broken down to glucose, whereas hemicellulose may be broken down to xylose, arabinose, mannose, galactose, and/or glucose. These sugars can then be converted to biofuel via microorganisms. For example, glucose can be fermented to produce an alcohol such as ethanol or butanol. While lignocellulosic biomass can be broken down into sugars solely using various chemical processes (e.g., acid hydrolysis), enzymatic hydrolysis is often the preferred approach for generating glucose as it is associated with higher yields, higher selectivity, lower energy costs, and milder operating conditions. For example, the cellulose in lignocellulosic biomass may be converted to glucose by cellulases. However, as a result of the complicated structure of the plant cell wall, the enzymatic digestibility of cellulose in native lignocellulosic biomass is often low unless a large excess of enzyme is used (e.g., lignocellulosic biomass may be considered recalcitrant to biodegradation). Unfortunately, the cost of suitable enzymes can be high, and can significantly contribute to the overall cost of the process. Accordingly, it is advantageous for enzymatic hydrolysis to be preceded by a pretreatment process that makes the lignocellulosic biomass more amenable to enzymatic hydrolysis and/or reduces the amount of enzyme required.

In general, a favorable pretreatment will reduce biomass recalcitrance (e.g., open up the structure of the lignocellulosic material, make the cellulose more accessible to the enzymes, and/or generally improve enzymatic digestibility of the cellulose) to an extent that enzyme loading and/or hydrolysis time is satisfactorily reduced (e.g., relative to no pretreatment), but without excessive production of degradation products. Some examples of pretreatment processes that have been used and/or proposed for preparing lignocellulosic biomass for enzymatic hydrolysis include physical pretreatment (e.g., milling and grinding), dilute acid pretreatment, alkali pretreatment (e.g., lime), ammonia fiber expansion, hot water extraction, steam explosion, organic solvent, and/or wet oxidation.

In dilute acid pretreatment, mineral acids such as sulfuric acid ($H_2SO_4$) hydrochloric acid (HCl), phosphoric acid ($H_3PO_4$), or nitric acid ($HNO_3$), are used to prepare the lignocellulosic biomass for enzymatic hydrolysis. Pretreating with acid under dilute conditions solubilizes the hemicellulose fraction of the lignocellulosic biomass, which can make the cellulose more accessible to the enzymes. Unfortunately, dilute acid pretreatment can produce degradation products (e.g., furfural, 5-hydroxymethylfurfural, phenolic acids, aldehydes, etc.) at a level that is potentially inhibitory and/or inactivating to downstream microorganisms. Moreover, since degradation products such as furfural are typically derived from xylose, the xylose yield following dilute acid pretreatment can be limited. In addition, the removal of lignin is limited, and most of the lignin (e.g., >70%) is retained in solids after the pretreatment.

In steam pretreatment, the lignocellulosic biomass typically is treated with high pressure saturated steam at a temperature (e.g., greater than 180° C.) and for a period of time selected to promote hemicellulose hydrolysis. If the pressure is quickly released, the lignocellulosic biomass undergoes an explosive decompression and the pretreatment may be referred to as steam explosion. Impregnating the lignocellulosic biomass with an acid (e.g., $H_2SO_4$, sulfur dioxide ($SO_2$), etc.) prior to steam pretreatment can lead to a more complete removal of hemicellulose during the steam pretreatment and/or increased enzymatic digestibility of the lignocellulosic biomass. However, as in dilute acid pretreatment, the xylose yield and removal of lignin may be limited. Moreover, acid-catalyzed steam explosion is often associated with lignin condensation.

Lignin has been identified as a culprit in reducing enzyme efficiency on pretreated lignocellulosic biomass, as it may act both as a physical barrier, restricting cellulose accessibility, and as a cellulase non-productive binder. Lignin has been linked to irreversible cellulase loss during pretreated lignocellulosic biomass saccharification. Pretreatment technologies such as lime pretreatment, aqueous ammonia pretreatment, or organosolv pretreatment, are reported as providing higher levels of lignin removal than dilute acid and/or steam explosion pretreatment. Nevertheless, steam explosion (e.g., in combination with dilute acids) remains the most commonly used pretreatment method as it is generally more effective in enhancing hydrolysis efficiency. It has been proposed that steam explosion pretreatment could be followed with a lignin-extraction process (e.g., organosolv treatment) in order to enhance digestibility of the lignocellulosic biomass; however, providing an additional lignin removal step introduces additional complications and/or cost.

As recognized in the pulp and paper industry, delignification processes can be energy-intensive and have costly chemical recovery. In general, the goal of pulping may be to remove as much lignin as possible without the concurrent loss and degradation of hemicellulose and cellulose, thus providing a pulp with high yield and strength. The sulfite pulping process is one of the oldest means of performing this operation, and was the predominant process until it was largely replaced by the sulfate or Kraft process. In sulfite pulping, various salts of sulfurous acid extract the lignin from woodchips in large pressure vessels called digesters (e.g., for 4-14 hours at temperatures ranging from 130 to 160° C.). Unfortunately, since the spent cooking liquor, which can be called brown or red liquor, contains bisulfite or sulfite salts (i.e., combined $SO_2$), there are recycling and/or recovery challenges associated with the process chemicals. Since one goal of pulping has been to retain the integrity of the hemicellulose and cellulose, it would appear unlikely that such methods would be suitable for pretreatment of lignocellulosic material. Nevertheless, in US Pub. No. 2015/

0299738, Wang et al. disclose sulfite pretreatment to overcome recalcitrance of lignocellulose (SPORL). In this pretreatment, the woody biomass is first treated with bisulfite or sulfite, and then in a second step, is fed to a mechanical disk miller. SPORL pretreatment has been reported to improve digestibility of lignocellulosic biomass by removing hemicellulose, partially dissolving lignin, and decreasing hydrophobicity of lignin by sulfonation. However, in sulfite pretreatments, such as SPORL, there is generally a tradeoff between increasing lignin dissolution and increasing hemicellulose dissolution. In particular, while lignin dissolution increases with increasing pH, hemicellulose dissolution decreases with increasing pH. Since sulfite pretreatments rely on a certain sulfurous acid salt concentration (i.e., require a certain amount of pulping cation), the pH of the cooking liquor is typically above 1.5, and is generally too high to maximize hemicellulose dissolution. In US Pub. No. 2015/0299738, Wang et al. rely on both a relatively high temperature (e.g., 180° C.) and an energy intensive post pretreatment mechanical size reduction in order to obtain an improvement in the digestibility of the woody biomass.

In U.S. Pat. No. 9,243,364, Zhu et al. disclose a two stage process including a first stage, where the lignocellulosic biomass is subjected to a bisulfite cook where the pH>3 (e.g., a neutral bisulfite cook) to promote delignification, and a second stage, where the pH of the solution is decreased (e.g., to a pH between 1 and 3 by adding $H_2SO_4$) in order to promote dissolution of hemicelluloses. In each of the first and second stages the pretreatment temperature is between 150° C. and 200° C., while the total pretreatment time in each stage is less than 90 minutes. In other words, this acid sulfite process, when used for pretreating lignocellulosic biomass, relies on temperatures greater than 150° C. Moreover, as with SPORL, this pretreatment relies on a certain sulfurous acid salt concentration, and thus may be accompanied by the same chemical recycling challenges as sulfite pulping.

In U.S. Publ. No. 2015/0225756, Retsina et al. disclose that the low solubility of $SO_2$ in water and low diffusion of water to wood necessitates the use of counter ions and several hours of cooking time, and that instead a heated aqueous alcohol and $SO_2$ can be used to rapidly dissolve lignin and hemicelluloses from wood. Unfortunately, this process includes a stripping and fractionation step where the cooking alcohol is removed from the spent liquor.

SUMMARY

It has recently been discovered that lignocellulosic biomass can be pretreated efficiently with $SO_2$, without adding extraneous pulping cations or organic solvent (e.g., alcohol). In particular, it was discovered that an effective pretreatment can be provided at a relatively low temperature when the total amount of $SO_2$ is greater than 20 wt % (based on dry weight of lignocellulosic biomass) and when the pretreatment time is greater than about 90 minutes (see U.S. Pat. Appl. No. 62/583,705). By increasing the amount of $SO_2$ used and providing relatively long pretreatment times, both lignin dissolution and hemicellulose dissolution were promoted. More specifically, lignin dissolution reached or exceeded about 50%, while the residual xylan reached about 5%.

It has now been discovered that the effectiveness of this pretreatment may be related to the concentration of lignosulfonic acid present in the pretreatment and/or that selecting the pretreatment conditions to provide a certain concentration of lignosulfonic acid may make the pretreatment more favorable.

In general, lignosulfonic acid may be generated in situ in an $SO_2$ pretreatment as the lignocellulosic biomass is sulfonated. Accordingly, the concentration of lignosulfonic acid in pretreatment may be selected, at least in part, by adjusting the total amount of $SO_2$ present, the pretreatment time, and/or the pretreatment temperature. For example, a concentration of lignosulfonic acid that is effective to improve pretreatment may be generated solely in situ in an $SO_2$ pretreatment wherein the total amount of $SO_2$ is greater than 20 wt % (based on dry weight of lignocellulosic biomass), the pretreatment temperature is between about 110° C. and 150° C., and the pretreatment time is greater than about 90 minutes. Alternatively, or additionally, the concentration of lignosulfonic acid in pretreatment may be selected, at least in part, by adding lignosulfonic acid to the pretreatment.

According to one aspect of the invention there is provided a process for converting lignocellulosic biomass to a fermentation product, said process comprising: providing the lignocellulosic biomass; subjecting the lignocellulosic biomass to a lignosulfonic acid pretreatment wherein the concentration of lignosulfonic acid is greater than 0.02 mol/L and wherein a total amount of sulfur dioxide is greater than 15 wt % based on dry weight of lignocellulosic biomass, said lignosulfonic acid pretreatment conducted between 110° C. and 150° C. for at least 30 minutes, thereby providing a pretreated slurry comprising cellulose; subjecting at least the cellulose to an enzymatic hydrolysis to provide glucose; subjecting at least the glucose to a microbial fermentation to produce the fermentation product; and, recovering the fermentation product.

According to one aspect of the invention there is provided a process for converting lignocellulosic biomass to a fermentation product, said process comprising: providing the lignocellulosic biomass; subjecting the lignocellulosic biomass to a lignosulfonic acid pretreatment wherein the concentration of lignosulfonic acid is greater than 0.02 mol/L, said pretreatment conducted for at least 30 minutes, thereby providing a pretreated slurry comprising cellulose; separating the pretreated slurry into a liquid stream and a solids stream, wherein the solids stream comprises cellulose and the liquid stream comprises xylose and lignosulfonate; feeding lignosulfonic acid obtained or derived from said liquid stream to the pretreatment reactor; subjecting the solids stream to an enzymatic hydrolysis that converts at least 60% of the cellulose in the lignocellulosic biomass to glucose; subjecting at least the glucose to a microbial fermentation to produce the fermentation product; recovering the fermentation product.

According to one aspect of the invention there is provided a process for converting lignocellulosic biomass to glucose, said process comprising: providing the lignocellulosic biomass; subjecting the lignocellulosic biomass to a lignosulfonic acid pretreatment wherein the concentration of lignosulfonic acid is greater than 0.02 mol/L and wherein a total amount of sulfur dioxide is greater than 15 wt % based on dry weight of lignocellulosic biomass, said lignosulfonic acid pretreatment conducted between 110° C. and 150° C. for at least 30 minutes, thereby providing a pretreated slurry comprising cellulose; subjecting at least the cellulose in the pretreated slurry to an enzymatic hydrolysis that converts at least 60% of the cellulose from the lignocellulosic biomass to glucose.

DETAILED DESCRIPTION

Figure 1:
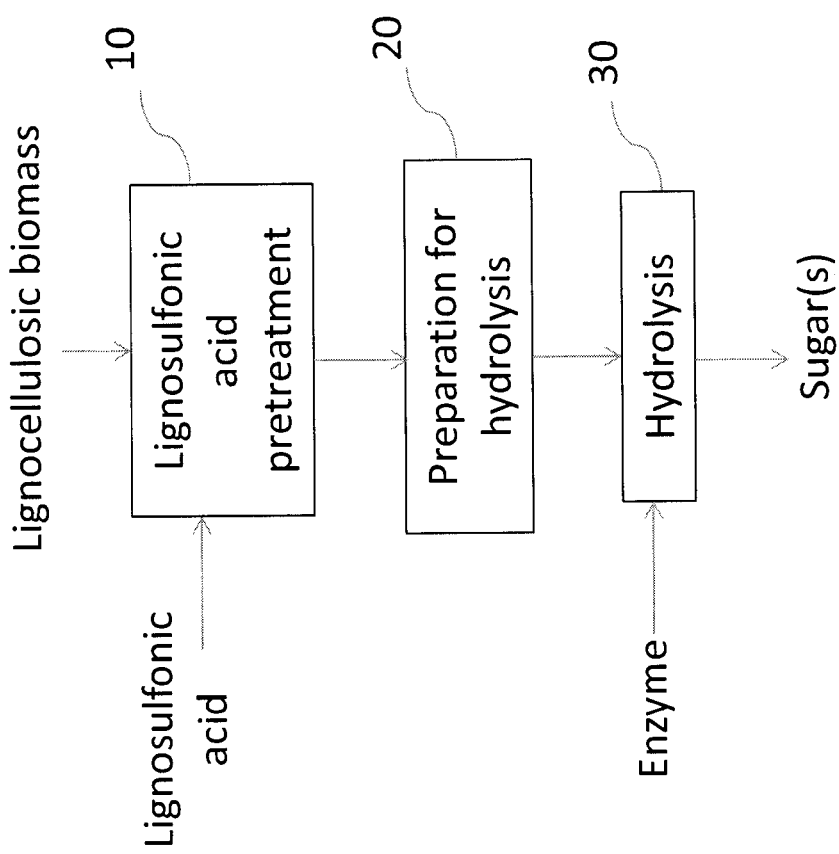
FIG. 1 is a block flow diagram of a process according to one embodiment of the invention, wherein lignocellulosic biomass is pretreated with lignosulfonic acid.

Unless defined otherwise, all technical and scientific terms used herein have the same meanings as commonly understood by one of ordinary skill in the art. For purposes of the present invention, the following terms are defined below.

The terms "a," "and," and "the" can include plural references unless the context clearly dictates otherwise. The terms "comprises", "comprising", "including", and/or "includes" are intended to mean "including but not limited to." The term "and/or" is intended to refer to either or both of the elements so conjoined. The term "at least one" in reference to a list of one or more elements, is intended to refer to at least one element selected from any one or more of the elements in the list of elements, but not necessarily including at least one of each and every element specifically listed within the list of elements. Thus, as a non-limiting example, the term "at least one of A and B" may refer to at least one A with no B present, at least one B with no A present, or at least one A and at least one B in combination. The terms "first," "second," etc., may be used to distinguish one element from another, and these elements should not be limited by these terms.

The term "lignocellulosic biomass" refers to any natural lignocellulosic material that includes lignin, cellulose, and hemicellulose (e.g., xylan). The term "raw lignocellulosic biomass" refers to lignocellulosic biomass that is close to its native (unprocessed) form, and includes lignocellulosic feedstock that has been processed by typical harvesting and preparatory techniques (e.g., size reduction, washing, sand removal, etc.). The term "raw lignocellulosic biomass" also encompasses biomass wherein water soluble compounds have been removed (e.g., includes bagasse, which is formed during the process of removing sucrose from sugar cane). In general, the cellulose, hemicellulose, and/or lignin in raw lignocellulosic biomass will not have been subject to significant chemical modification.

The term "lignin" generally refers to the matrix of phenolic polymers found in the cell walls of many plants. The composition and/or structure of lignin can vary depending on the plant source and/or any methods used to separate it from the cell walls. The term "lignin", as used herein, refers to the intact lignin structure found in the cell walls of plants and/or fragments or compounds derived therefrom resulting from disruption of the lignin structure. In particular, the term "lignin", as used herein, includes soluble lignin or derivatives of the lignin, condensed lignin, and insoluble unreacted lignin.

The term "sulfonated lignin" refers to lignin into which sulfonic acid groups and/or sulfonate groups have been introduced. For example, sulfonated lignin can be produced by reacting lignin with sulfur dioxide, a bisulfite, and/or or a sulfite at elevated temperatures. Alternatively, sulfonated lignin may be produced by subjecting lignin to a sulfomethylation reaction.

The term "lignosulfonate" or "lignosulfonates" refers to water soluble sulfonated lignin (i.e., soluble in water at neutral and/or acid conditions). For example, water solubility may be imparted when sulfonic acid and/or sulfonate groups are incorporated within lignin in an amount effective to solubilize the lignin. The terms "lignosulfonate" or "lignosulfonates", as used herein, encompasses both lignosulfonic acid and its neutral salts.

The term "lignosulfonic acid" refers to lignosulfonate wherein a significant number of the sulfonate groups on the lignin are protonated (—$SO_3H$) or fully dissociated (—$SO_3^-$), without being bound to a salt-forming cation (e.g., such that a solution or slurry thereof has a pH less than 7).

The terms "concentration of lignosulfonic acid" or "concentration of LSA" are interchangeable and refer to the concentration of sulfonate groups on the lignin that are in acid form (i.e., protonated or fully dissociated, and not bound with a salt-forming cation and/or metal). The concentration of lignosulfonic acid may be expressed in moles per liter of solution or slurry.

The terms "concentration of lignosulfonic acid salts", "concentration of lignosulfonate salts", or "concentration of LSS" are interchangeable and refer to the concentration of sulfonate groups on lignin that are in salt form (i.e., where the sulfonate group is associated with a salt-forming counter ion). The salt forming counter ion(s) may originate from base, sulfite salt, or bisulfite salt added during the process (e.g., $Na^+$ from NaOH, $Na_2SO_3$, or $NaHSO_3$, respectively), and may for example, include calcium ($Ca^{2+}$), ammonium ($NH_4^+$), magnesium ($Mg^{2+}$), and/or sodium ($Na^+$).

The term "pretreatment" refers to one or more steps conducted prior to enzymatic hydrolysis to open up the structure of the lignocellulosic material, make the cellulose more accessible to the enzymes, and/or generally improve enzymatic digestibility of the cellulose. Pretreatment can lead to at least partial removal and/or separation of hemicellulose from cellulose, and/or at least partial degradation and/or removal of lignin.

The term "$SO_2$ pretreatment" refers to an acid pretreatment wherein the lignocellulosic biomass is in contact with sulfur dioxide. Sulfur dioxide ($SO_2$) is a gas, which when dissolved in water, may be referred to as sulfurous acid ($H_2SO_3$). The term "sulfur dioxide" or "$SO_2$", as used herein, includes $SO_2$ in the gas phase, $SO_2$ in the liquid phase, and/or $SO_2$ dissolved in an aqueous solution or slurry.

The term "acid pretreatment" refers to a pretreatment conducted in the presence of at least one acid, and generally has an initial pH that is below 2.0. The term "acid pretreatment", as used herein is distinct from sulfite pretreatments, acid sulfite pretreatments, bisulfite pretreatments, and/or organosolv-type pretreatments, in that to the extent any base, sulfite salt, and/or bisulfite salt is added to the process for the pretreatment it is added in an amount that is less than 1.5 wt % (based on dry weight of incoming lignocellulosic biomass), and to the extent any organic solvent is added to the process for the pretreatment it is added in an amount that is less than 5 wt % (based on dry weight of incoming lignocellulosic biomass).

The term "lignosulfonic acid pretreatment" refers to an acid pretreatment conducted in the presence of lignosulfonic acid. The lignosulfonic acid may be generated in situ and/or added.

The term "initial pH", as used herein, refers to the pH of the slurry immediately prior to pretreatment (i.e., after all of the acid to be added to pretreatment has been added). Initial pH can be measured, or can be calculated based on the amount of acid added and other factors (e.g., presence of innate alkalinity in the feedstock). The initial pH is measured at ambient temperature on-line or from a sample taken after all of the acid and lignocellulosic biomass has been added, but before heating above 100° C.

The term "final pH", as used herein, refers to the pH of the pretreated slurry, which is obtained after the pretreatment. For example, if the pretreatment is a multistage pretreatment, the final pH is measured after the last stage. Final pH is measured at ambient temperature on-line or from a sample taken after the pretreated material is discharged from the pretreatment reactor(s). In instances where the pretreated slurry has a large undissolved solids content and/or is relatively thick, the final pH is measured from a filtrate, pressate, or centrate of the sample (e.g., or other liquid from a solids-liquid separation) that is cooled to ambient temperature.

The terms "consistency" and "solids consistency" are interchangeable and refer to the weight of insoluble solids per weight of slurry, expressed as a percentage. More specifically, the term "consistency" refers to the amount of undissolved dry solids or "UDS" in a sample expressed as a weight percentage, % (w/w), also denoted herein as wt %.

The term "slurry" refers to a mixture of insoluble material and a liquid. In most cases, the liquid includes water and may include dissolved solids. For example, pretreated biomass typically is provided as a slurry. In some instances, for example in slurries having a consistency greater than about 15%, the visual presence of free liquid may not be evident.

The term "stream", as used herein, refers to a gas, liquid, or solid, or any combination thereof, moving or en route from one location to another. A stream is still a stream even if it is temporarily stationary. Accordingly, the term "stream" is applicable when referencing materials in both batch and continuous processes. Reference to a stream or material, refers to any portion of the stream or material, including the stream or material in its entirety. A portion of a stream or material may be mixed with other compositions of matter and the mixture will be considered to comprise the portion of the original stream or material. In some cases, the composition of a stream may vary as it passes through one or more stages of the process. The terms "upstream" and "downstream", as used herein, refer to a relative point/stage in the process with respect to a reference point/stage. For example, the term "upstream" refers to a point/stage that occurs 'before' the reference point/stage, whereas the term "downstream" refers to a point/stage that occurs 'after' the reference point/stage.

In accordance with embodiment of the instant invention, lignocellulosic biomass is pretreated with lignosulfonic acid that is generated in situ in an $SO_2$ pretreatment as the lignocellulosic biomass is sulfonated, and/or is added to the pretreatment. In one embodiment, the concentration of lignosulfonic acid in pretreatment is selected, at least in part, by adjusting the total amount of $SO_2$ present, the pretreatment time, and/or the pretreatment temperature. Adjusting the pretreatment conditions to ensure that the concentration of lignosulfonic acid reaches a particular level (e.g., 0.02 mol/L) can lower the pretreatment time and/or total amount of $SO_2$ required to provide the desired pretreatment level. For example, adding lignosulfonic acid may allow pretreatments conducted with a total amount of $SO_2$ that is less than 20 wt % (e.g., about 15 wt %, or higher) to be effective. Alternatively, increasing the total amount of $SO_2$ may increase the concentration of lignosulfonic acid generated in situ to a level effective to reduce the required pretreatment time (e.g., to about 30 minutes, or higher). Notably, this reduction in the amount of $SO_2$ required and/or pretreatment time can be achieved without adding base, sulfite salt, bisulfite salt, or organic solvent (e.g., ethanol).

Advantageously, when lignocellulosic biomass mass is pretreated with both a relatively high concentration of lignosulfonic acid (e.g., greater than about 0.02 mol/L) and a relatively high total amount of $SO_2$ (e.g., greater than about 15 wt % based on dry weight of lignocellulosic biomass), both hemicellulose and lignin dissolution can be increased. The use of relatively high amounts of $SO_2$ promotes lignin sulfonation, which provides the lignin with a strong hydrophilic structure, and facilitates lignin dissolution. The generation and/or addition of lignosulfonic acid, in the absence of a large concentration of salt-forming cations, can result in a significant number of the sulfonate groups on lignin being in acid form (e.g., not in salt form). The formation and/or addition of lignosulfonic acid, wherein a significant number of the sulfonate groups are in acid form, is advantageous, for example, in that: 1) sulfonic acids are strong acids that can promote hemicellulose dissolution; 2) it can reduce the amount of acid added into the process and/or facilitate the recovery/recycle of process chemicals; and/or 3) it can facilitate the recovery of lignosulfonates.

With regard to the first point, it has been discovered that pretreatment with a relatively high amount of $SO_2$, without a large concentration of salt-forming cation, can produce a pH drop of about 0.2 units from the start to the end of the pretreatment process. For example, when sufficient $SO_2$ is added to the lignocellulosic biomass to produce a slurry with a pH of about 1.2 (i.e., the initial pH), pretreatment can result in a pretreated slurry having a pH of about 1.0 (i.e., the final pH). Advantageously, this pH drop is provided largely by the formation of lignosulfonic acid, without requiring extraneous acid. Further advantageously, since lignosulfonic acid is a strong acid, it may be about as effective as $H_2SO_4$ or HCl with regard to hemicellulose dissolution, and thus can replace such acids where required. Moreover, lignosulfonic acid is a much stronger acid than sulfurous acid, as individual sulfonic acids have a pKa below zero. Therefore, producing even a modest amount of lignosulfonic acid makes it the dominant acid, even in a system with a large concentration of sulfurous acid. Since lignosulfonic acid is a stronger acid than $H_2SO_3$ its production during pretreatment further drives hemicellulose dissolution. Advantageously, even though lignosulfonic acid is a strong acid, it is less corrosive than $H_2SO_4$ or HCl at a given pH, and is generally associated with fewer corrosion and/or safety issues than mineral acids. Further advantageously, although lignosulfonic acid promotes hemicellulose dissolution, xylose may be relatively stable in its presence. Accordingly, both a high xylose yield and a high hemicellulose dissolution can be achieved.

With regard to the second point (i.e., reducing the amount of acid added into the process and/or facilitating the recovery/recycle of process chemicals), consider the case where at least part of the lignosulfonic acid is generated in situ. In this case, the $SO_2$ is essentially used twice, first to sulfonate the lignin, and second as a sulfonic acid. At the end of pretreatment, unreacted $SO_2$, including any dissolved $SO_2$, can be released, whereas the lignosulfonic acid remains in solution. Since the $SO_2$ is released as a gas (e.g., from flashing) it can be collected, recovered, and/or recycled directly. Since the lignosulfonic acid is relatively stable, it can also be recycled within the process. Recycling the lignosulfonic acid provides the means to reduce the pH in pretreatment without having to add additional $SO_2$, or having to add a mineral acid such as HCl or $H_2SO_4$. Advantageously, the pH is lowered with what may be considered a by-product of the pretreatment. Accordingly, using such lignosulfonic acid does not introduce new chemicals or compounds into the pretreatment. Since no new chemicals are introduced, chemical recovery is simpler. For example, if $H_2SO_4$ was added instead to reduce the pH (e.g., as in some sulfite pulping-type pretreatments), subsequent neutralization with lime may produce large quantities of calcium sulfate (gypsum), which requires additional energy and expense for disposal. In addition, acid recovery costs for the instant process may be reduced since acid recovery may also be tied to lignosulfonate recovery.

With regard to the third point (i.e., facilitating lignosulfonate recovery), the acid functionality of the lignosulfonic acid may be used to facilitate at least partial purification of the lignosulfonic acid and/or may simplify the recovery process.

Certain exemplary embodiments of the invention now will be described in more detail, with reference to the drawings, in which like features are identified by like reference numerals. The invention may, however, be embodied in many different forms and should not be construed as limited to the embodiments set forth herein.

Referring to FIG. 1, there is shown a process in accordance with one embodiment of the invention. Lignocellulosic biomass is subjected to a pretreatment with lignosulfonic acid 10, which includes heating the lignocellulosic biomass in the presence of lignosulfonic acid. The pretreated material is then prepared 20 for hydrolysis (e.g., filtered, washed, cooled, and/or pH adjusted) and at least the solid fraction thereof is hydrolyzed 30 with added enzyme. The hydrolysis 30 produces sugar(s) (e.g., the cellulose in the pretreated material is converted to glucose).

In this embodiment, the lignosulfonic acid is added to the pretreatment, either with the lignocellulosic biomass and/or separately. For example, in one embodiment, the lignocellulosic biomass is contacted with the lignosulfonic acid prior to being fed to the pretreatment reactor. The lignosulfonic acid that is added to the pretreatment may be extraneous to the process (e.g., sourced from a sulfite pulping process or a commercial product) or may be generated on site. For example, when generated on site the lignosulfonic acid may be produced from the lignocellulosic biomass in a separate dedicated process, or may be recycled from elsewhere in the process. The lignosulfonic acid may be added as a solid or a liquid. For example, in one embodiment lignosulfonic acid is added as an aqueous solution having a pH less than 3, less than 2, or less than 1. Advantageously, providing the lignosulfonic acid as an aqueous solution having a pH less than about 1, or more preferably less than about 0.8, allows the lignosulfonic acid to better promote hemicellulose dissolution without adding an excessive amount of water. In one embodiment, the lignosulfonic acid is generated from a substantially neutral lignosulfonate salt product by passing the same through a cation exchange resin in the $H^+$ form to reduce the pH to about 0.7, or lower.

Figure 2:
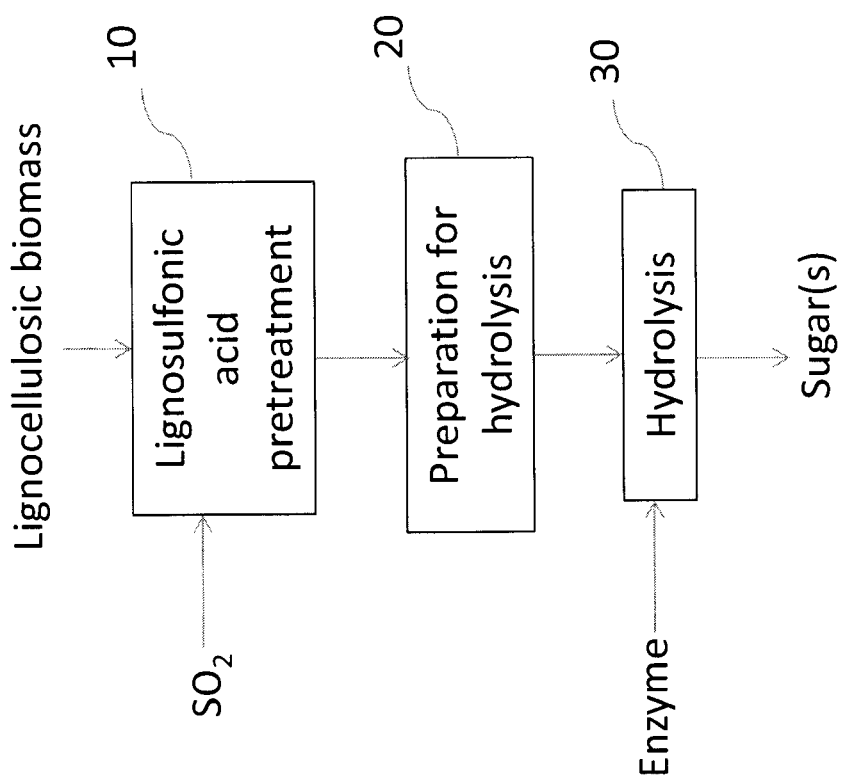
FIG. 2 is a block flow diagram of a process according to one embodiment of the invention, wherein lignocellulosic biomass is pretreated with lignosulfonic acid generated in situ.

Referring to FIG. 2, there is shown a process in accordance with another embodiment of the invention. As in the embodiment described with reference to FIG. 1, lignocellulosic biomass is subjected to a pretreatment with lignosulfonic acid 10. The pretreated material is then prepared 20 for hydrolysis (e.g., filtered, washed, cooled, and/or pH adjusted) and at least the solid fraction thereof is hydrolyzed 30 with added enzyme. The hydrolysis 30 produces sugar(s) (e.g., the cellulose in the pretreated material is converted to glucose).

In this embodiment, the lignosulfonic acid is produced in situ as a result of the addition of $SO_2$ to the lignocellulosic biomass (i.e., where the total amount of $SO_2$ present is greater than about 20 wt % (w/w based on dry weight of incoming lignocellulosic biomass)). The $SO_2$ may be added to the pretreatment either with the lignocellulosic biomass and/or separately. For example, in one embodiment, the lignocellulosic biomass is soaked in an aqueous solution of sulfurous acid prior to being fed to the pretreatment reactor. In one embodiment, sufficient $SO_2$ is added to provide an initial pH that is less than about 1.5, less than about 1.25, or less than about 1. In one embodiment, sufficient $SO_2$ is added to provide a final pH that is less than about 1.5, less than about 1.25, less than about 1, or less than about 0.8. In one embodiment, sufficient $SO_2$ is added to produce an amount of lignosulfonic acid effective to reduce the pH of the slurry by at least 0.25 units relative to the initial pH, within 30 minutes.

Advantageously, generating the lignosulfonic acid in situ means that the only pretreatment chemical that needs to be added to the lignocellulosic biomass is $SO_2$, which is readily added as a gas. Adding pretreatment chemical as a gas may provide a more uniform pretreatment. In addition, generating the lignosulfonic acid in situ by the addition of $SO_2$ also allows the lignocellulosic biomass to be simultaneously pretreated with $SO_2$ (i.e., an $SO_2$ pretreatment). As described in U.S. Pat. Appl. No. 62/583,705, it has been discovered that lignocellulosic biomass can be pretreated efficiently with $SO_2$, without adding extraneous pulping cations or organic solvent. In particular, it was discovered that an effective pretreatment can be provided at relatively low temperatures when the total amount of sulfur dioxide is greater than 20 wt % based on dry weight of lignocellulosic biomass and when the pretreatment time was greater than about 90 minutes. Under these conditions, a sufficient concentration of sulfonate groups in the acid form can be generated during the first 30 minutes of pretreatment to cause the pH to drop more than 0.25 units. Accordingly, the $SO_2$ not only sulfonates the lignin, thereby increasing lignin dissolution, but also forms lignosulfonic acid, which can increase hemicellulose dissolution.

Figure 3:
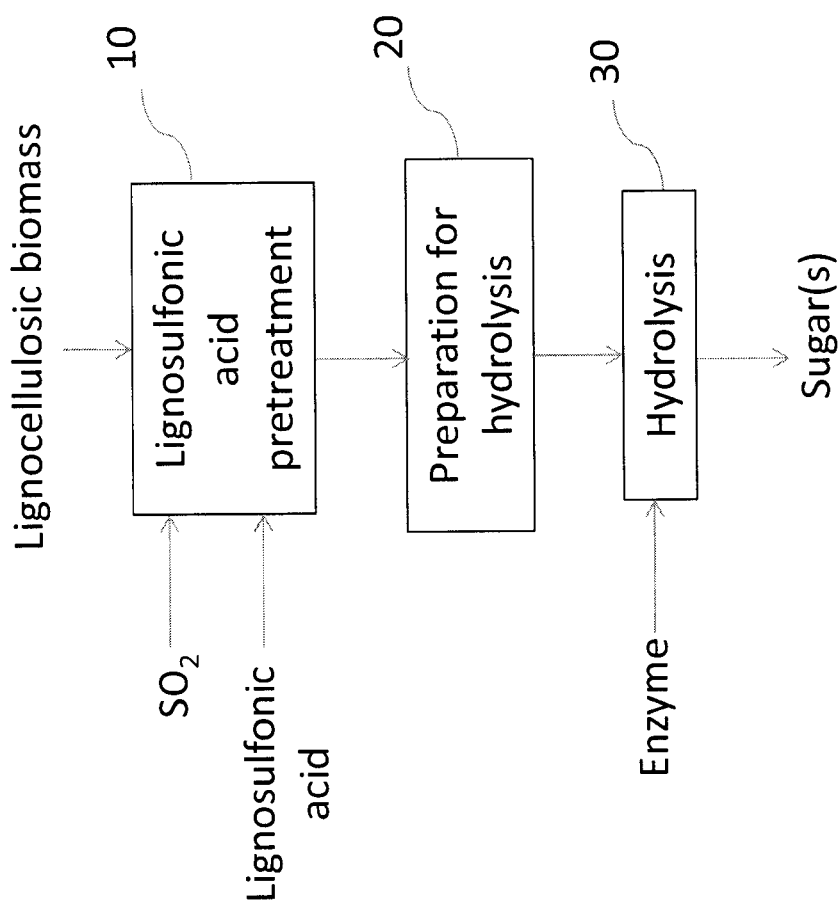
FIG. 3 is a block flow diagram of a process according to one embodiment of the invention, wherein lignocellulosic biomass is pretreated with sulfur dioxide and lignosulfonic acid.

Referring to FIG. 3, there is shown a process in accordance with another embodiment of the invention. As in the embodiment described with reference to FIG. 1, lignocellulosic biomass is subjected to a pretreatment with lignosulfonic acid 10. The pretreated material is then prepared 20 for hydrolysis (e.g., filtered, washed, cooled, and/or pH adjusted) and at least the solid fraction thereof is hydrolyzed 30 with added enzyme. The hydrolysis 30 produces sugar(s) (e.g., the cellulose in the pretreated material is converted to glucose).

In this embodiment, the lignosulfonic acid is both fed to the pretreatment and generated in situ (e.g., as a result of the addition of $SO_2$). As disclosed in U.S. Pat. Appl. No. 62/583,705, it has been discovered that a good pretreatment can be achieved when the total amount of $SO_2$ present is greater than about 20 wt %. When lignosulfonic acid is added, this amount of $SO_2$ can be reduced and/or the pretreatment time reduced, while still providing a good pretreatment. More specifically, the lignosulfonic acid will further drive down the pH and increase hemicellulose dissolution, while the $SO_2$ increases lignin dissolution. Notably, adding lignosulfonic acid to further drive down the pH is advantageous over using mineral acids such as HCl and/or $H_2SO_4$ for the following reasons: 1) it simplifies chemical recovery (i.e., lignosulfonic acid is generated in situ with $SO_2$ pretreatment, so adding additional lignosulfonic acid does not complicate chemical recovery); 2) lignosulfonic acid is less corrosive than HCl and/or $H_2SO_4$ at similar pH values; and 3) xylose may be more stable in the presence of lignosulfonic acid than these mineral acids, particularly at elevated temperatures, and therefore may result in a relatively high xylose yield.

Although lignosulfonic acid is a strong acid, to the best knowledge of the instant inventors, adding it to a process to catalyze pretreatment as described herein has not been previously considered. One reason for this may be that lignosulfonic acid can have a relatively high average molecular weight, a varied composition, and/or be relatively complex—thus making it difficult to know what is added and introducing concerns about consistency. To date, the structure of lignin has not been exactly defined (e.g., is often discussed in terms of prominent substructures). In addition, lignosulfonates may possess a certain degree of surface activity and have been associated with dispersive, stabilizing, binding, and/or complexing properties—properties that can introduce unpredictability and/or that can change with pretreatment conditions. Another reason is that the concentration of $SO_2$ used in most previous studies was too low to produce an effective amount of sulfonate groups in acid form. Moreover, it is not obvious how introducing a very strong acid and/or additional lignin would affect lignin dissolution and/or xylose yield.

Advantageously, since this configuration uses $SO_2$, which promotes lignin sulfonation, and lignosulfonic acid, which promotes hemicellulose dissolution, both a high lignin dissolution and high hemicellulose dissolution (e.g., residual xylan less than 10%) is achieved in some embodiments.

Figure 4:
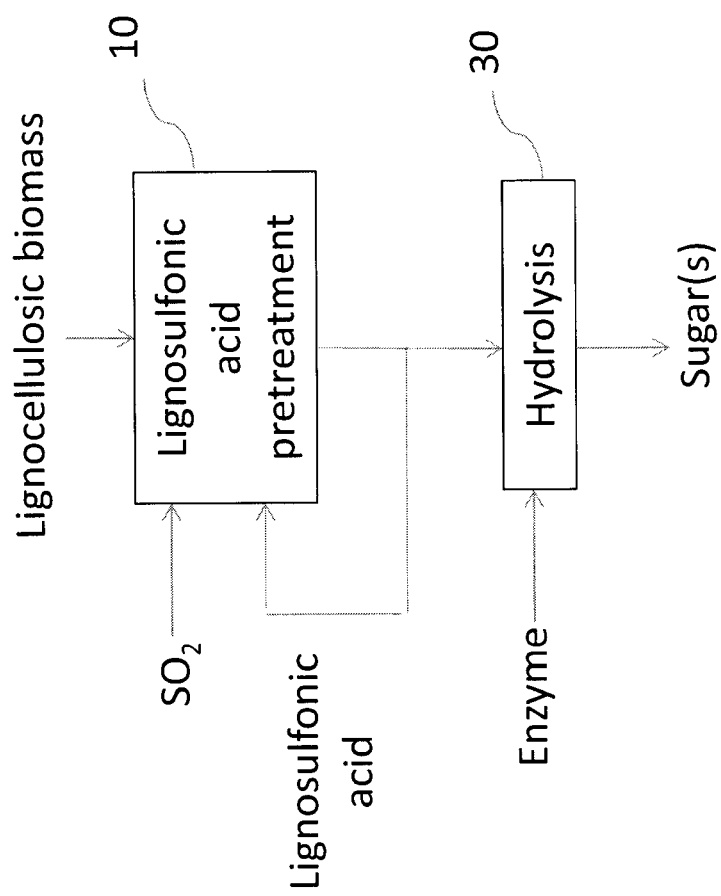
FIG. 4 is a block flow diagram of a process according to one embodiment of the invention, wherein lignocellulosic biomass is pretreated with recycled lignosulfonic acid.

Referring to FIG. 4, there is shown a method in accordance with another embodiment of the invention. As in the embodiment described with reference to FIG. 3, lignocellulosic biomass is subjected to a pretreatment with lignosulfonic acid 10, which includes heating the lignocellulosic biomass in the presence of lignosulfonic acid and $SO_2$. The pretreated material is then prepared for hydrolysis (e.g., filtered, washed, cooled, and/or pH adjusted) and at least the solid fraction thereof is hydrolyzed 30 with added enzyme. The hydrolysis 30 produces sugar(s) (e.g., the cellulose in the pretreated material is converted to glucose).

In this embodiment, the added lignosulfonic acid is introduced into pretreatment when a portion of the pretreated biomass is redirected back to the pretreatment (e.g., as a slip stream). In this case, both soluble and insoluble components of the pretreated slurry are fed back to pretreatment. In one embodiment, the fraction of pretreated biomass (e.g., 5% to 20% by volume) redirected back to pretreatment is selected to provide the pH desired for pretreatment. Advantageously, the pretreated biomass fed back to pretreatment can be split from the main stream before the main stream is prepared for hydrolysis. For example, in one embodiment, the pretreated material is fed back to pretreatment after flashing, but before being filtered, washed, cooled, and/or pH adjusted. While it is uncommon to recycle pretreated biomass back to a pretreatment reactor, as it may increase the amount of degradation products and/or cause the material to be overcooked, in this case the protective nature of the sulfonated lignin may lessen the risk of overcooking. Advantageously, since the lignosulfonic acid originates within the process, this embodiment provides the ability to reduce the initial pH without adding additional acid (e.g., $SO_2$, HCl, $H_2SO_4$) or by adding a smaller amount than would otherwise be needed.

Figure 5:
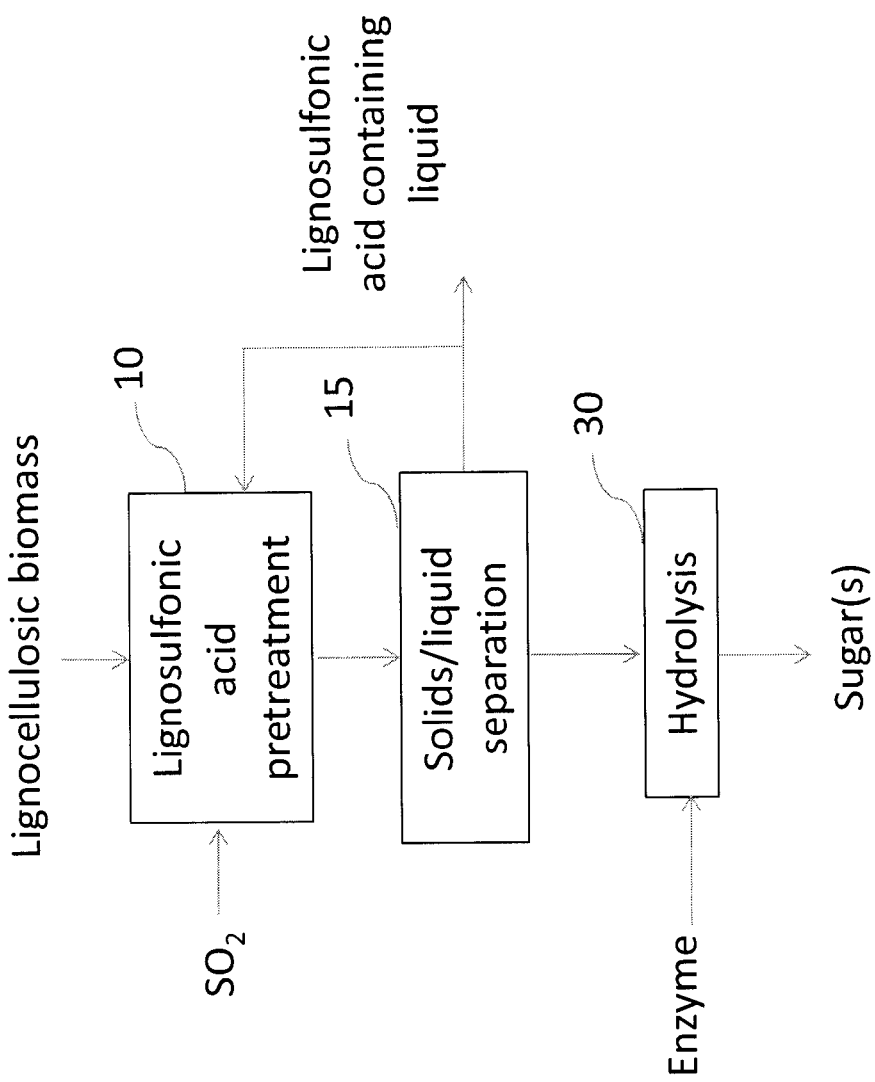
FIG. 5 is a block flow diagram of a process according to another embodiment of the invention, wherein lignocellulosic biomass is pretreated with recycled lignosulfonic acid.

Referring to FIG. 5, there is shown a process in accordance with another embodiment of the invention. As in the embodiment described with reference to FIG. 4, lignocellulosic biomass is subjected to a pretreatment with lignosulfonic acid 10, which includes heating the lignocellulosic biomass in the presence of lignosulfonic acid and $SO_2$. However, in this embodiment, the pretreated material is first subject to a solids-liquid separation 15, with the solids being fed to hydrolysis 30, and at least a portion of the liquid being returned to the pretreatment 10. In one embodiment, the solids are washed, cooled, slurried, and/or pH adjusted prior to, or as part of, the hydrolysis process 30. Since the liquid from the solids/liquid separation 15 contains lignosulfonic acid, in addition to other water soluble compounds such as xylose, this liquid stream is a source of additional lignosulfonic acid. In one embodiment, the fraction of the liquid stream (e.g., 5-20% by volume) redirected back to pretreatment is selected to provide the pH desired for pretreatment. Optionally, this recycled liquid stream is first contacted with a cation exchange resin. The remaining liquid is optionally subject to one or processing steps. For example, in one embodiment, the remaining liquid stream is neutralized and a) dried to provide a value-added lignosulfonate product, or b) fed to a step that at least partially separates the lignosulfonate from the sugars. In embodiments where the lignosulfonate is at least partially separated from the sugar(s), the sugar stream, which may be largely xylose, may be a) fed to a fermentation step that produces ethanol, b) fed to anaerobic digestion to produce biogas, and/or c) used for xylitol production. In embodiments where the lignosulfonate is produced for energy production and/or biogas is produced and used within the process, the greenhouse gas emissions of the process may be reduced.

Advantageously, this configuration allows a higher glucose yield relative to the configuration in FIG. 4, as the pretreated solids (e.g., which contain cellulose) are not returned to pretreatment where they can become overcooked and/or excessively degraded. As with the configuration illustrated in FIG. 4, this configuration advantageously provides the ability to reduce the initial pH without adding extraneous acid (e.g., apart from $SO_2$) or to use less acid. Further advantageously, this configuration may allow the concentration of lignosulfonic acid and/or xylose to build up, thus making recovery thereof more economical.

Figure 6:
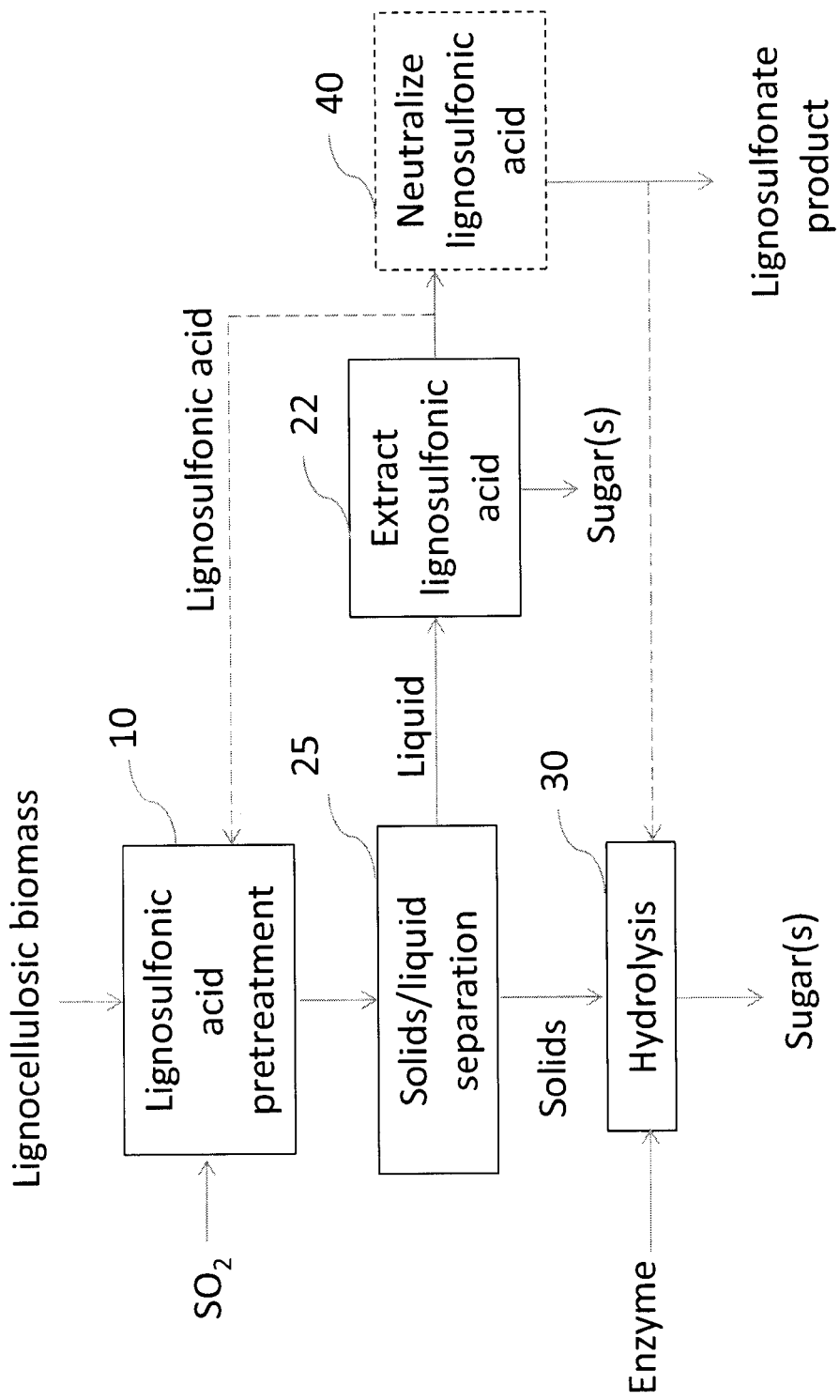
FIG. 6 is a block flow diagram of a process according to one embodiment of the invention, wherein lignocellulosic biomass is pretreated with at least partially purified recycled lignosulfonic acid.

Referring to FIG. 6, there is shown a process in accordance with another embodiment of the invention. In this embodiment, lignocellulosic biomass is subjected to a pretreatment with lignosulfonic acid 10, which includes heating the lignocellulosic biomass in the presence of lignosulfonic acid and $SO_2$. The lignosulfonic acid may be generated in situ and/or recycled (e.g., see dashed line). Following pretreatment 10, the pretreated material is subject to a solids-liquid separation 15, where the solids are fed to hydrolysis 30. For example, in one embodiment, the solids are washed, cooled, slurried, and/or pH adjusted prior to, or as part of, the hydrolysis process 30. At least a portion of the liquid from the solids/liquid separation 15, which includes lignosulfonic acid in addition to other water soluble compounds such as xylose, is fed to a lignosulfonic acid extraction stage 22 of the process. In this separation stage 22, the lignosulfonic acid is at least partially separated from the sugar(s). The sugar stream may be used and/or provided for any suitable application. For example, in one embodiment, at least a portion of the sugar stream is a) fed to anaerobic digestion to produce biogas, b) fed to a fermentation tank that contains microorganisms that convert xylose to ethanol, c) fed to a fermentation tank that contains microorganisms that can co-ferment glucose and xylose to produce ethanol, d) converted to a furanic fuel, and/or e) used to produce xylose and/or xylitol. The lignosulfonic acid stream may also be used and/or provided for any suitable application. For example, in this embodiment, a portion of the lignosulfonic acid stream is optionally recycled back to pretreatment 10, while the remaining portion is optionally neutralized 40 and/or otherwise processed to provide a lignosulfonate product (e.g., value-added or for energy production). Optionally, this recycled liquid stream is first contacted with a cation exchange resin. In addition, in this embodiment, at least some lignosulfonate is optionally added to enzymatic hydrolysis in order to enhance hydrolysis. For example, lignosulfonate (e.g., neutralized to about pH 4.8) may enhance enzymatic processing of lignocellulosic material by reducing non-specific binding of enzyme to lignin and enhancing enzymatic activity. In embodiments, where the lignosulfonate is produced for energy production and/or biogas is produced and used within the process, the greenhouse gas emissions of the process may be reduced.

As with the configurations illustrated in FIGS. 4 and 5, this configuration advantageously provides the ability to reduce the initial pH without adding extraneous acid (e.g., apart from $SO_2$) or adding less acid than would otherwise be needed. However, this configuration may allow a higher xylose yield than that obtainable with the configuration illustrated in FIG. 5, as the pentose sugars are not returned to pretreatment 10 where they can be degraded.

This configuration is particularly advantageous when xylose from the pretreatment is fermented to provide ethanol. For example, when ethanol is generated from both glucose (e.g., derived from cellulose) and the xylose (e.g., derived from the hemicellulose), the ethanol yield for the process can be increased. In addition, as the step of extracting the lignosulfonic acid 22 increases the pH of the xylose-containing liquid, the extracting step can reduce or eliminate the amount of strong base needed to prepare the xylose containing liquid for fermentation microorganisms.

In addition, since this configuration includes an extracting step 22, which provides a xylose containing stream, the lignosulfonate stream can be purer than that typically obtained from sulfite pulping processes. Further advantageously, since the lignosulfonate is extracted as an acid, a specific counter ion may be readily introduced into the lignosulfonate. In any case, since the process uses a relatively high amount of $SO_2$ and/or since this configuration facilitates some of the xylose being converted to ethanol, the quantity and/or quality of marketable products available can be increased (e.g., ethanol yield can be increased and a highly marketable lignosulfonate can be produced).

Figure 7:
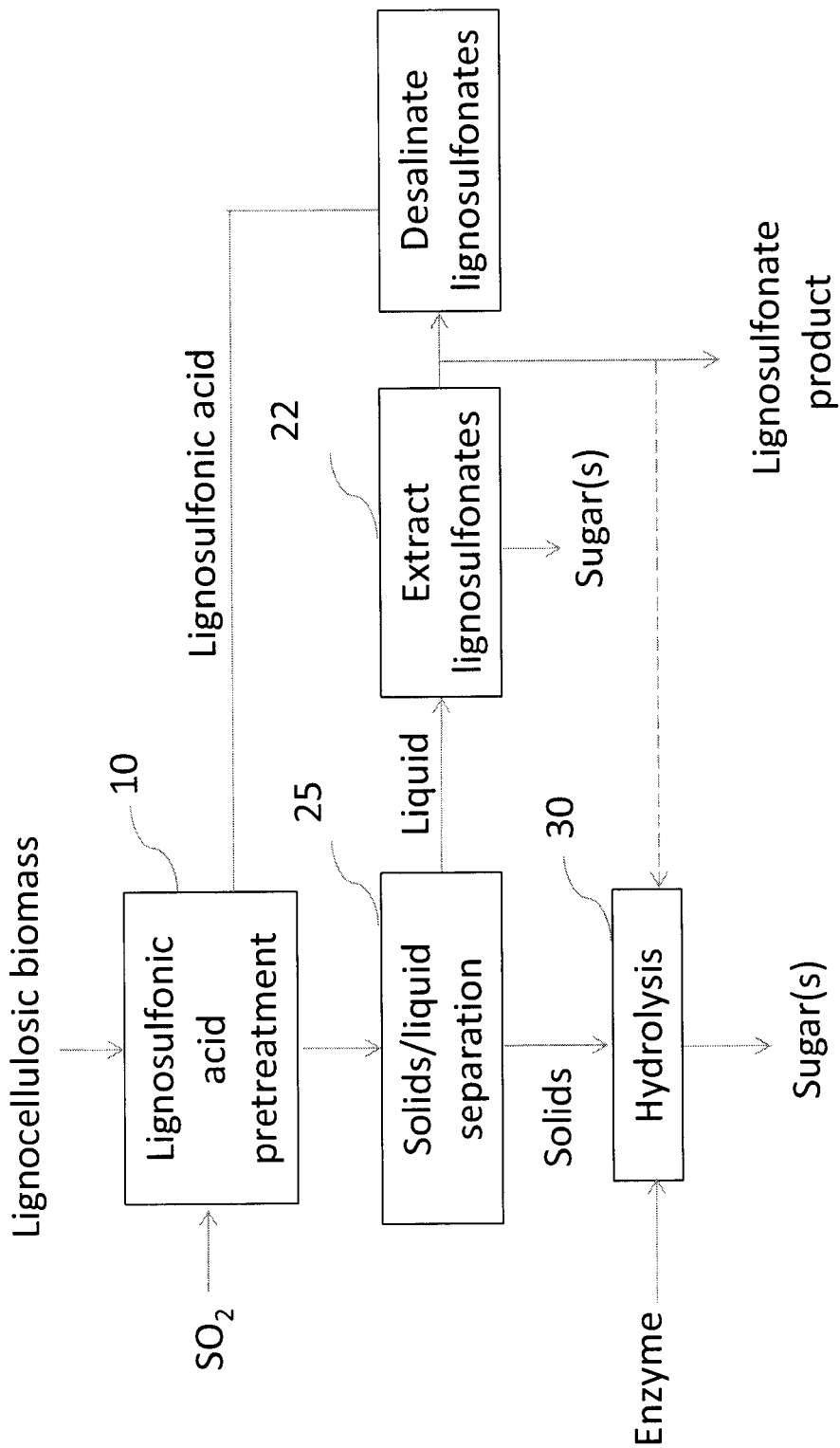
FIG. 7 is a block flow diagram of a process according to another embodiment of the invention, wherein lignocellulosic biomass is pretreated with at least partially purified recycled lignosulfonic acid.

Referring to FIG. 7, there is shown a process in accordance with another embodiment of the invention. In this embodiment, lignocellulosic biomass is subjected to a pretreatment with lignosulfonic acid 10, which in this case includes heating the lignocellulosic biomass in the presence of lignosulfonic acid and $SO_2$. Following pretreatment 10, the pretreated material is subject to a solids-liquid separation 15, where the solids are fed to hydrolysis 30. For example, in one embodiment, the solids are washed, cooled, slurried, and/or pH adjusted prior to, or as part of, the hydrolysis process 30. At least a portion of the liquid from the solids/liquid separation 15, which includes lignosulfonic acid in addition to other water soluble compounds such as xylose, is fed to a lignosulfonate extraction stage 22 of the process. In this separation stage 22, the lignosulfonate is separated at least partially from the sugar(s). The sugar stream may be used and/or provided for any suitable application. For example, in one embodiment, at least a portion of the sugar stream is a) fed to anaerobic digestion to produce biogas, b) fed to a fermentation tank that contains microorganisms that convert xylose to ethanol, c) fed to a fermentation tank that contains microorganisms that can co-ferment glucose and xylose to produce ethanol, d) used to produce furanic fuels, and/or e) used to produce xylose and/or xylitol. The lignosulfonate stream may also be used and/or provided for any suitable application. For example, in this embodiment, a portion of the lignosulfonate stream is desalinated (e.g., contacted with a cation exchange resin to remove cations) and recycled back to pretreatment 10, while the remaining portion is provided as a lignosulfonate product (e.g., value-added or for energy production). In addition, in this embodiment, at least some lignosulfonate is optionally added to enzymatic hydrolysis 30 in order to enhance hydrolysis. In embodiments, where the lignosulfonate is produced for energy production and/or biogas is produced and used within the process, the greenhouse gas emissions of the process may be reduced.

As with the configurations illustrated in FIGS. 4, 5, and 6, this configuration advantageously provides the ability to reduce the initial pH without adding extraneous acid (e.g., apart from $SO_2$) or adding less than would otherwise be needed. Advantageously, this configuration allows the lignosulfonate to be recovered using techniques proven in commercial sulfite pulping processes (e.g., Howard and ultrafiltration), while still facilitating the recycling of lignosulfonic acid.

In each of the embodiments described with reference to FIGS. 1 to 7, hexose(s) produced from enzymatic hydrolysis 30 (e.g., C6 sugars such as glucose) and/or or pentose(s) produced during pretreatment 10 (e.g., C5 sugars such as xylose) may be further processed. For example, the C5 and/or C6 sugars may be converted to a biofuel or fuel additive, or may be used to produce a bioproduct (e.g., a bioplastic).

In one embodiment, the process further includes fermenting the C6 sugar produced during the hydrolysis 30 to an alcohol (not shown). In general, this fermentation may be a separate fermentation step or part of a simultaneous hydrolysis/fermentation. In one embodiment, this fermentation includes fermenting glucose to ethanol using yeast (*Saccharomyces cerevisiae*). In one embodiment, this fermentation includes fermenting glucose to butanol. In one embodiment, this fermentation includes fermenting glucose in addition to pentose sugars produced during pretreatment using microbe(s) that can ferment both glucose and pentose sugars. In one embodiment, the method further includes a step of recovering the alcohol (not shown).

In embodiment, the process further includes converting the C5 sugars to a biofuel or fuel additive (e.g., ethanol, butanol, a furanic fuel, biogas, etc.). Advantageously, using the C5 sugars to produce ethanol can increase the ethanol yield for the process. In one embodiment, the C5 sugars are used to produce xylitol.

Lignocellulosic Biomass

In general, the lignocellulosic biomass fed to the pretreatment may include and/or be derived from any lignocellulosic feedstock that needs to be pretreated in order to improve enzymatic digestibility.

Some examples of suitable lignocellulosic feedstock include: (i) energy crops; (ii) residues, byproducts, or waste from the processing of plant biomass in a facility or feedstock derived therefrom; (iii) agricultural residues; (iv) forestry biomass; (v) waste material derived from pulp and paper products; (vi) pulp and paper waste; and/or (vii) municipal waste including components removed from municipal waste.

Energy crops include biomass crops such as grasses, including C4 grasses, such as switch grass, energy cane, sorghum, cord grass, rye grass, miscanthus, reed canary grass, C3 grasses such as *Arundo donax*, or a combination thereof.

Residues, byproducts, or waste from the processing of plant biomass include residues remaining after obtaining sugar from plant biomass (e.g., sugar cane bagasse, sugar cane tops and leaves, beet pulp, Jerusalem artichoke residue), and residues remaining after grain processing (e.g., corn fiber, corn stover, and bran from grains). Agricultural residues include, but are not limited to soybean stover, corn stover, sorghum stover, rice straw, sugar cane tops and/or leaves, rice hulls, barley straw, wheat straw, canola straw, oat straw, oat hulls, corn fiber, and corn cobs.

Forestry biomass includes hardwood, softwood, recycled wood pulp fiber, sawdust, trimmings, and/or slash from logging operations. Pulp and paper waste includes waste from chemical pulping such as black liquor, spent sulfite liquor, sludge, and/or fines.

Municipal waste includes post-consumer material or waste from a variety of sources such as domestic, commercial, institutional and/or industrial sources. For example, in one embodiment, the lignocellulosic feedstock includes refuse from waste collection and/or sewage sludge.

In one embodiment, the lignocellulosic feedstock is an energy or biomass crop. In one embodiment, the lignocellulosic feedstock comprises an agricultural residue. In one embodiment, the lignocellulosic feedstock comprises a non-woody lignocellulosic feedstock. In one embodiment, the lignocellulosic feedstock comprises hardwood. In one embodiment, the lignocellulosic feedstock comprises wheat straw, or another straw. In one embodiment, the lignocellulosic feedstock comprises stover. As used herein, the term "straw" refers to the stem, stalk and/or foliage portion of crops remaining after the removal of starch and/or sugar containing components for consumption. Examples of straw include, but are not limited to sugar cane tops and/or leaves, bagasse, oat straw, wheat straw, rye straw, rice straw and barley straw. The term "stover" includes the stalk and foliage portion of crops after the removal of starch and/or sugar containing components of plant material for consumption. Examples of stover include, but are not limited to, soybean stover, sorghum stover, and corn stover. In one embodiment, the lignocellulosic feedstock is a mixture of fibers that originate from different kinds of plant materials, including mixtures of cellulosic and non-cellulosic feedstocks. In one embodiment, the lignocellulosic feedstock is a second generation feedstock.

Biomass Preparation

In general, the lignocellulosic biomass may be subjected to one or more optional preparatory steps prior to the pretreatment and/or as part of the pretreatment. Some examples of biomass preparation include size reduction, washing, leaching, sand removal, soaking, wetting, slurry formation, dewatering, plug formation, addition of heat, and addition of chemicals (e.g., pretreatment and/or other). In general, these preparatory steps may depend on the type of biomass and/or the selected pretreatment conditions.

In one embodiment, the lignocellulosic biomass is subjected to a size reduction. Some examples of size reduction methods include milling, grinding, agitation, shredding, compression/expansion, and/or other types of mechanical action. Size reduction by mechanical action may be performed by any type of equipment adapted for the purpose, for example, but not limited to, hammer mills, tub-grinders, roll presses, refiners, hydropulpers, and hydrapulpers. In one embodiment, lignocellulosic feedstock having an average particle size that is greater than about 6-8 inches is subject to a size reduction wherein at least 90% by volume of the particles produced from the size reduction have a length between about 1/16 inch and about 6 inches.

In one embodiment, the lignocellulosic biomass is washed and/or leached with a liquid (e.g., water and/or an aqueous solution). Washing, which may be performed before, during, or after size reduction, may remove sand, grit, fine particles of the lignocellulosic feedstock, and/or other foreign particles that otherwise may cause damage to the downstream equipment. Leaching, which may be performed before, during, or after size reduction, may remove soluble components from the lignocellulosic feedstock. Leaching may remove salts and/or buffering agents.

In one embodiment, the lignocellulosic biomass is subject to sand removal. For example, in one embodiment, the lignocellulosic biomass is washed to remove sand. Alternatively, or additionally, sand may be removed using other wet or dry sand removal techniques that are known in the art (e.g., including the use of a hydrocyclone or a sieve).

In one embodiment, the lignocellulosic biomass is slurried in liquid (e.g., water), which allows the lignocellulosic biomass to be pumped. In one embodiment, the lignocellulosic biomass is slurried subsequent to size reduction, washing, and/or leaching. The desired weight ratio of water to dry biomass solids in the slurry may be determined by factors such as pumpability, pipe-line requirements, and other practical considerations. In general, slurries having a consistency less than about 10 wt % may be pumped using a relatively inexpensive slurry pump.

In one embodiment, the lignocellulosic biomass is soaked in water and/or an aqueous solution (e.g., comprising a pretreatment chemical). Soaking the lignocellulosic biomass may allow pretreatment chemical(s) to more uniformly impregnate the biomass, which in turn may provide even cooking in the heating step of pretreatment. For example, soaking the feedstock in a solution comprising a pretreatment chemical (e.g., such as lignosulfonic acid and/or sulfurous acid) typically provides uniform impregnation of the biomass with the pretreatment chemical. Soaking the feedstock in water, may allow gaseous pretreatment chemicals (e.g., sulfur dioxide) to more uniformly and/or completely impregnate the lignocellulosic biomass during subsequent chemical addition steps. In general, soaking may be carried out at any suitable temperature and/or for any suitable duration.

In one embodiment, the lignocellulosic biomass is wet with a liquid (e.g., water or an aqueous solution) or steam in order to moisten the lignocellulosic biomass and provide a desired consistency. Providing lignocellulosic biomass with a higher consistency to pretreatment may advantageously reduce heating requirements (e.g., since there is less liquid to heat).

In one embodiment, the lignocellulosic biomass is at least partially dewatered (e.g., to provide a specific consistency). In one embodiment, the lignocellulosic biomass is at least partially dewatered in order to increase the undissolved solids content relative to the incoming biomass. In one embodiment, the lignocellulosic biomass is at least partially dewatered in order to remove at least some of the liquid introduced during washing, leaching, slurrying, and/or soaking. In one embodiment, dewatering is achieved using a drainer, filtration device, screen, screw press, and/or extruder. In one embodiment, dewatering is achieved using a centrifuge. In one embodiment, the dewatering is achieved prior to and/or as part of plug formation. In general, plug formation may be considered an integration of lignocellulosic biomass particles into a compacted mass referred to herein as a plug. Plug formation devices may or may not form a plug that acts as a seal between areas of different pressure. Some examples of plug formation devices that dewater biomass include a plug screw feeder, a pressurized screw press, a co-axial piston screw feeder, and a modular screw device.

As mentioned above, each of the washing, leaching, slurrying, soaking, dewatering, and preheating stages are optional and may or may not be included in the process. In general, if the process is a continuous-flow process, it may be advantageous to include steps of slurrying and dewatering prior to pretreatment in order to improve process economics and efficiency. In addition, providing soaking, preheating, and chemical addition steps upstream of the acid pretreatment may provide a more uniform and/or efficient acid pretreatment.

Pretreatment

In general, the pretreatment includes subjecting the lignocellulosic biomass to a pretreatment with lignosulfonic acid. Lignosulfonic acid, which may be formed by the sulfonation of lignin during sulfite pulping and/or an $SO_2$-based pretreatment, is a water soluble mixture of compounds. For example, being derived from lignin, lignosulfonic acid may include sulfonated lignin monomers, oligomers, and/or polymers. Examples of lignin monomers are the phenolic compounds p-hydroxyphenol, guaiacol, and syringyl alcohol, which contain 0, 1, or 2 methoxyl groups, respectively. The relative amount of each type of monomer in lignin typically varies among feedstocks: softwood lignin, for example, is especially high in syringyl groups. In lignosulfonic acid, each oligomer and/or polymer may contain more than one sulfonate group (e.g., the sulfonate group is typically substituted onto the alpha carbon of the side chain). Accordingly, the properties of lignosulfonic acid may be dependent on the lignin source, the degree of polymerization (e.g., average number of monomers per oligomer/polymer), molar mass distribution, the degree of sulfonation (e.g., number of sulfonate groups per oligomer/polymer), and/or the presence of counter ions such as $Ca^{2+}$, $Mg^{2+}$, $Na^+$, $NH4^+$, etc.

As lignosulfonic acid can vary in molecular weight and degree of sulfonation, the amount of the lignosulfonic acid present in the pretreatment can be quantified using the "concentration of lignosulfonic acid", which refers to the concentration of sulfonate groups on lignin that are in acid form (i.e., protonated and/or dissociated, but not bound to a salt-forming cation and/or metal). For example, the concentration of lignosulfonic acid can be determined by subtracting the concentration of cations from the total concentration of sulfonate groups on lignin.

In one embodiment, the lignosulfonic acid pretreatment is conducted in the presence of lignosulfonic acid, where the concentration of lignosulfonic acid is at least about 0.02 mol/L. In one embodiment, the concentration of lignosulfonic acid pretreatment is at least about 0.04 mol/L, 0.06 mol/L, 0.08 mol/L, or 0.1 mol/L. In one embodiment, the concentration of lignosulfonic acid is between 0.02 mol/L and 0.5 mol/L. In one embodiment, the concentration of lignosulfonic acid is between 0.05 mol/L and 0.3 mol/L. In one embodiment, the concentration of lignosulfonic acid is about 0.1 mol/L.

In one embodiment, the lignosulfonic acid pretreatment includes heating the lignocellulosic biomass with lignosulfonic acid at one or more temperatures between about 110° C. and about 170° C. In one embodiment, the lignosulfonic acid pretreatment includes heating the lignocellulosic biomass with lignosulfonic acid at one or more temperatures between about 110° C. and about 160° C. In one embodiment, the lignosulfonic acid pretreatment includes heating the lignocellulosic biomass with lignosulfonic acid at one or more temperatures between about 110° C. and about 150° C. Conducting the lignosulfonic acid pretreatment at these relatively low temperatures advantageously avoids the specialized equipment and/or xylose degradation associated with pretreatments at relatively high temperatures (e.g., greater than 160° C.).

In one embodiment, the lignosulfonic acid pretreatment includes heating the lignocellulosic biomass with lignosulfonic acid at one or more temperatures between about 110° C. and about 150° C., for more than 30 minutes. In one embodiment, the lignosulfonic acid pretreatment includes heating the lignocellulosic biomass with lignosulfonic acid at one or more temperatures between about 110° C. and about 150° C., for more than 60 minutes, or more than 90 minutes.

In one embodiment, the pretreatment time, temperature, and the concentration of lignosulfonic acid is selected to convert most of the hemicellulose component to soluble sugars (e.g., xylose, mannose, arabinose, and glucose), but little of the cellulose component to sugars (e.g., which may be hydrolyzed in a subsequent enzymatic hydrolysis). For example, in one embodiment, the degree of pretreatment is selected such that the amount of xylan hydrolyzed to xylose is greater than about 50 wt %, about 60 wt %, about 70 wt %, about 80 wt %, or about 90 wt %. In one embodiment, the concentration of lignosulfonic acid is selected to be effective to provide a residual xylan level that is less than about 8 wt %.

In general, the lignosulfonic acid present in pretreatment may be generated in situ, may be produced for the pretreatment, may be obtained from a recycle stream, and/or may be a commercial product. For example, some examples of commercial lignosulfonate include Borresperse NA and Borresperse CA (Borregaard).

In embodiments where the lignosulfonic acid is added to the pretreatment (i.e., not solely generated in situ), it may be added as an aqueous solution. In order to ensure that the concentration of lignosulfonic acid is within the desired range during the pretreatment, an aqueous solution containing lignosulfonate salts may be first contacted with a strong acid cation exchange resin. For example, a strong cation exchange resin that contains sulfonate functional groups (i.e., with an affinity for protons or metal cations) can strip salt-forming cations from the lignosulfonate and replace them with protons, thereby yielding lignosulfonic acid having a low pH (e.g., generally below 2, typically below 1, and often as low as 0.5). In one embodiment, a commercial lignosulfonate, a recovered lignosulfonate, or a recycle stream containing lignosulfonic acid is contacted with a cation exchange resin to provide lignosulfonic acid having a pH less than about 1, prior to being added to the pretreatment reactor. In one embodiment, the amount of lignosulfonic acid and/or degree of protonation of the sulfonate groups is selected to provide an initial pH that is less than 1.5, less than 1.25, or less than 1.

In general, in embodiments where $SO_2$ is present in the lignosulfonic acid pretreatment, it will sulfonate the lignocellulosic biomass to produce lignosulfonic acid. Accordingly, the concentration of lignosulfonic acid, which may be dependent on the added lignosulfonic acid and/or lignosulfonic acid generated in situ, is measured at the end of pretreatment (e.g., after removing the pretreated biomass from the pretreatment reactor). In one embodiment, the amount of $SO_2$ added and/or the concentration of the lignosulfonic acid added to pretreatment, is effective to provide a final pH that is less than 1.5, less than 1.25, less than 1, or less than 0.75. In one embodiment, wherein both $SO_2$ and lignosulfonic acid are added, more than 30% of the total acidity [$H^+$] present is provided by the lignosulfonic acid. In one embodiment, wherein both $SO_2$ and lignosulfonic acid are added, more than 40%, 50%, 60%, or 70% of the total acidity [$H^+$] present is provided by the lignosulfonic acid.

In embodiments wherein the lignosulfonic acid is solely generated in situ, a concentration of lignosulfonic acid that is greater than 0.02 mol/L may be provided when the total amount of sulfur dioxide present is greater than 20 wt %, the pretreatment time is greater than 90 minutes, the pretreatment temperature is between 110 and 150° C., and the consistency of the lignocellulosic biomass prior to pretreatment is between 10 wt % and 30 wt %. The term "total amount of sulfur dioxide", as used herein, refers to the total amount of sulfur dioxide provided for the pretreatment per amount of lignocellulosic biomass on a dry weight basis. In general, the "total amount of sulfur dioxide" is calculated from the grams of sulfur dioxide present initially per gram of dry weight of lignocellulosic biomass present (e.g., as a weight percentage (wt %)). For example, if 25 g of gaseous sulfur dioxide is added to 100 g of lignocellulosic biomass having total solids (TS) content of 93.25% (e.g., 6.75% moisture content), the total amount of sulfur dioxide is calculated as follows:

$$\text{Total amount } SO2 =$$

$$\frac{\text{g } SO2 \text{ added}}{\text{g biomass added} * TS \text{ content}} = \frac{25 \text{ g } SO2}{(100 \text{ g biomass}) * 0.9325} = 27 \text{ wt \%}$$

Alternatively, if 52 mL of sulfurous acid prepared to be about 6% (w/w) $H_2SO_3$ is added to 6.43 g of lignocellulosic biomass having a total solids (TS) content of 93.25% (e.g., 6.75% moisture content), the total amount of sulfur dioxide is calculated as:

$$\text{Total amount } SO2 = \frac{\text{g } SO2 \text{ added}}{\text{g biomass added} * TS \text{ content}} =$$

$$\frac{\text{volume } H2SO3 \text{ (mL) added} * \text{density of } H2SO3 \left(\frac{\text{g}}{\text{mL}}\right) * \frac{6 \text{ g}}{100 \text{ g}} * \frac{Mw \; SO2}{Mw \; H2SO3}}{\text{g biomass added} - TS \text{ content}} =$$

$$\frac{52 * 1.03 * 6 * 64.066 / (100 * 82.07)}{6.43 * 0.9325} = 42 \text{ wt \%}$$

In some cases, the total amount of sulfur dioxide can be represented by the sulfur dioxide loading. The term "sulfur dioxide loading" is often used for continuous systems, where it refers to the amount of sulfur dioxide fed to the pretreatment system per amount of dry lignocellulosic biomass fed to the pretreatment system (e.g., calculated from the grams of sulfur dioxide provided per gram of dry weight lignocellulosic biomass (e.g., as a weight percentage (wt %)). However, in some cases, the total amount of sulfur dioxide can be higher than the sulfur dioxide loading (e.g., if some $SO_2$ is held within the pretreatment system when the pretreated lignocellulosic biomass is discharged). For example, in PCT Application No. PCT/CA2016/051089, filed on Sep. 16, 2016, a pretreatment system having a charge of $SO_2$ is disclosed. In this case, the total amount of sulfur dioxide provided includes the amount of sulfur dioxide provided in the charge of $SO_2$.

In embodiments wherein the lignosulfonic acid is both added and generated in situ, a concentration of lignosulfonic acid that is between about 0.04 and 0.2 mol/L may provide good hemicellulose dissolution.

The concentration of lignosulfonic acid may be calculated as follows. Following pretreatment, the pretreated slurry is cooled down and filtered (e.g., vacuum-filtered using glass microfiber filter paper). The filtrate is collected and analyzed to determine the concentration of lignosulfonic acid, which is calculated by subtracting the concentration of cations (denoted "A") from the total concentration of sulfonate groups on lignin (denoted "B").

The concentration of cations (A) in the pretreated filtrate, expressed in moles/liter, may be measured by ion chromatography. The cations measured are $Na^+$ (sodium), $K^+$ (potassium), $NH_4^+$ (ammonium), $Ca^{2+}$ (calcium), and $Mg^{2+}$ (magnesium). More specifically, the concentration of cations may be measured on a Metrohm 881 Compact IC pro equipped with a Metrohm 858 Professional Sample Processor autosampler, Metrosep C 4 150/4.0 column and guard, and conductivity detector. The cations are quantified against a standard curve using cation standards (Absolute Standards Inc.) containing 200 mg/L of $Na^+$, $K^+$, $NH_4^+$, $Ca^{2+}$, and $Mg^{2+}$ in water.

The total concentration of sulfonate groups on lignin (B) in the pretreated filtrate, expressed in moles/liter, may be derived from a sulfur analysis. More specifically the total concentration of sulfonate groups on lignin can be obtained by subtracting the sulfur contributions from unreacted sulfurous acid (denoted "C") from the total sulfur concentration (denoted "D").

The total sulfur concentration (D) in the pretreatment filtrate, expressed in moles/liter, can be measured by combustion, as per ATSM Method D 4239-04, Method B-High-Temperature combustion method with infrared absorption procedure. The total sulfur concentration (D) accounts for sulfur from unreacted sulfurous acid and the lignosulfonic acid.

The sulfur contributions from unreacted sulfurous acid (C) can be measured as an inorganic sulfate concentration following a treatment that oxidizes any sulfite present to sulfate (i.e., $SO_4^{2-}$). For example, this treatment may include transferring 7.9 mL of 200 mM NaOH, 100 μL of pretreatment filtrate, and 2 mL of 3% $H_2O_2$, to a Metrohm sample vial, via mechanical pipette. The mixture is then vortexed. The concentration of inorganic sulfate (C) in the treated filtrate can be determined using ion chromatography (i.e., on a Metrohm 881 Compact IC pro, equipped with a Metrohm 858 Professional Sample Processor autosampler, Metrosep A Supp 5 150/4.0 column and guard, and an IC conductivity detector with suppression). Anions are quantified against a standard curve using anion standards (Absolute Standards Inc.) containing 200 mg/L $Cl^-$ (chloride), $PO_4^{3-}$ (phosphate), and $SO_4^{2-}$ (sulfate) in water.

Accordingly, the concentration of lignosulfonic acid is calculated as

=B(total concentration of sulfonate groups on lignin)−A(concentration of cations)

=D(total sulfur concentration)−C(sulfate concentration)−A(concentration of cations), expressed in mol/L. When the concentration of cations (A) is greater than the total concentration of sulfonate groups on lignin (B), then the concentration of lignosulfonic acid is zero. The concentration of lignosulfonate salt is the smaller of B and A.

In general, the pretreatment may be carried out in batch mode, semi-batch mode, or continuous mode, in one or more pretreatment reactors. For example, the pretreatment may be conducted in one or more vertical reactors, horizontal reactors, inclined reactors, or any combination thereof.

In one embodiment, the pretreatment is carried out in batch mode in a steam autoclave. In one embodiment, the pretreatment is conducted in a plug flow reactor. In one embodiment, the pretreatment is conducted in a counter-current flow reactor. In one embodiment the pretreatment is conducted in a reactor provided with a charge of sulfur dioxide as described in as illustrated in PCT Application No. PCT/CA2016/051089, filed on Sep. 16, 2016.

In one embodiment, the pretreatment is conducted in a pretreatment system, which may include a plurality of components/devices in addition to a pretreatment reactor. Some examples of these devices/components include a biomass conveyer, washing system, dewatering system, a plug formation device, a heating chamber, a high shear heating chamber, a pre-steaming chamber, an $SO_2$ impregnation chamber, vapour reservoir chamber, an additional pretreatment reactor, connecting conduits, valves, pumps, etc.

In one embodiment, the pretreatment is conducted in a pretreatment system and/or reactor that is pressurizable. For example, in one embodiment, the pretreatment reactor and/or pretreatment system includes a plurality of valves and/or other pressure increasing, pressure decreasing, or pressure maintaining components for providing and/or maintaining the pretreatment reactor at a specific pressure.

In general, the pretreatment is conducted in a pretreatment system and/or pretreatment reactor that includes a heater, or some other heating means, for heating the lignocellulosic biomass to the pretreatment temperature. For example, in one embodiment, the pretreatment reactor is clad in a heating jacket. In another embodiment, the pretreatment reactor and/or the pretreatment system includes direct steam injection inlets. In one embodiment, the lignocellulosic biomass is heated (e.g., directly or indirectly) in the pretreatment reactor. In one embodiment, the lignocellulosic biomass is heated both upstream of and in the pretreatment reactor. In any case, direct steam injection may be advantageous in terms of quickly and uniformly heating high consistency biomass and/or for breaking down the biomass structure via steam explosion (e.g., if used).

In one embodiment, the pretreatment includes adding sulfur dioxide and/or sulfurous acid to the lignocellulosic material, which may be in the form of freshly-added $SO_2$, make-up $SO_2$, and/or recycled $SO_2$ (e.g., recycled from previous pretreatment reactions). The $SO_2$ may be added to the lignocellulosic biomass before entering the pretreatment reactor, within the pretreatment reactor, or a combination thereof. For example, the $SO_2$ may be added to the lignocellulosic biomass via separate inlets or via the same inlet. For example, in one embodiment, the lignocellulosic biomass is soaked in an aqueous sulfurous acid solution prior to entering the pretreatment reactor. In one embodiment, an aqueous slurry of lignocellulosic biomass is fed to the pretreatment reactor and gaseous sulfur dioxide is injected therein (e.g., bubbled into the slurry). In one embodiment, a slurry of lignocellulosic biomass and sulfurous acid is fed into the pretreatment reactor, and the pressure is increased by adding gaseous sulfur dioxide. In one embodiment, an aqueous slurry of lignocellulosic biomass is fed to the pretreatment reactor and liquid sulfur dioxide is injected therein.

At the end of the pretreatment, the pretreated lignocellulosic biomass will be removed/discharged from the pretreatment reactor and/or system. In one embodiment, this includes reducing the pressure on the pretreated lignocellulosic biomass. In general, the pressure may be released slowly or quickly. Alternatively, the pressure may be reduced at a stage further downstream. In one embodiment, the pressure is reduced by flashing.

Preparing the Pretreated Biomass for Enzymatic Hydrolysis

In general, the lignosulfonic acid pretreated material is subject to one or more steps to prepare it for hydrolysis, if required. For example, in one embodiment the pretreated material is subject to a pressure reduction, liquid/solid separation (e.g., filtering), a washing step, a cooling step, and/or a pH adjustment step.

In one embodiment, the lignosulfonic acid pretreated biomass is subject to a pressure reduction. For example, in one embodiment, the pressure is reduced using one or more flash tanks in fluid connection with the pretreatment reactor. Flashing may reduce the temperature of the pretreated biomass to 100° C. if an atmospheric flash tank is used, or lower if a vacuum flash tank is used.

In one embodiment, the lignosulfonic acid pretreated biomass is subject to a liquid/solid separation, which provides a solid fraction and a liquid fraction. The solid fraction may contain undissolved solids such as unconverted cellulose and/or insoluble lignin. The liquid fraction, which may also be referred to as the xylose-rich fraction, may contain soluble compounds such as sugars (e.g., xylose, glucose, and arabinose), organic acids (e.g., acetic acid and glucuronic acid), lignosulfonates, soluble sugar degradation products (e.g., furfural, which may be derived from C5 sugars, and hydroxymethylfurfural (HMF), which may be derived from C6 sugars) and/or one or more salts (e.g., sulfite salts). For example, in one embodiment, the pretreated biomass is flashed and then fed to one or more centrifuges that provide a solid stream and a liquid stream.

In one embodiment, the lignosulfonic acid pretreated biomass is subject to one or more washing steps. For example, in one embodiment, the solid fraction from a solid/liquid separation is washed to remove soluble components, including potential inhibitors and/or inactivators. Washing may also remove lignin (e.g., including lignosulfonates). In one embodiment, the pretreated biomass is washed as part of the liquid/solid separation (e.g., as part of decanter/wash cycle). The pretreated biomass may be washed as part of the liquid/solid separation at high or low pressure, which may or may not reduce the temperature of the pretreated biomass.

In one embodiment, the lignosulfonic acid pretreated biomass is subjected to one or more cooling steps. For example, in one embodiment, the pretreated biomass is cooled to within a temperature range compatible with enzyme(s) added for the enzymatic hydrolysis. For example, conventional cellulases often have an optimum temperature range between about 40° C. and about 60° C., and more commonly between about 50° C. and 55° C., whereas thermostable and/thermophilic enzymes may have optimum temperatures that are much higher (e.g., as high as, or greater than 80° C.). In one embodiment, the pretreated biomass is cooled to within a temperature range compatible with enzyme(s) and yeast used in a simultaneous saccharification and fermentation (SSF).

In one embodiment, cooling is provided primarily from flashing. In one embodiment, cooling is provided primarily using a heat exchanger. In one embodiment, cooling is provided primarily by washing the solids. In one embodiment, cooling is provided by any combination of flashing, heat exchange, washing, and other cooling techniques. In one embodiment, cooling is provided by injecting a fluid into the pretreated biomass. For example, in one embodiment, cooling is achieved when alkali and/or water is added to the pretreated biomass in order to provide the pH and/or consistency desired for enzymatic hydrolysis.

Advantageously, since the lignosulfonic acid pretreatment is conducted at relatively low temperatures (e.g., between 110° C. and 150° C.), the one or more cooling steps may not have to produce a significant temperature drop.

In one embodiment, the lignosulfonic acid pretreated biomass is subjected to one or more pH adjustment steps. In one embodiment, the pH of the pretreated biomass is adjusted to within a range near the pH optimum of the enzyme(s) used in hydrolysis. For example, cellulases typically have an optimum pH range between about 4 and about 7, more commonly between about 4.5 and about 5.5, and often about 5. In one embodiment, the pH is adjusted to between about 4 and about 8. In one embodiment, the pH is adjusted to between about 4.5 and about 6. In one embodiment, the pH is adjusted so as to substantially neutralize the pretreated biomass.

In one embodiment, the pH of the lignosulfonic acid pretreated biomass is increased as a result of the washing step. In one embodiment, the pH of the pretreated biomass is increased by adding alkali (e.g., calcium hydroxide, potassium hydroxide, sodium hydroxide, ammonia gas, etc.). For example, in one embodiment, sufficient alkali is added to increase the pH of the pretreated biomass to a pH near the optimum pH range of the enzyme(s) used in hydrolysis. In one embodiment, the pH adjustment step includes adding sufficient alkali to overshoot the optimum pH of the enzyme (e.g., overliming), and then adding acid to reduce the pH to near the optimum pH range of the enzyme(s).

In general, the pH adjustment step may be conducted on the solid fraction, the liquid fraction, and/or a combination thereof, and may be conducted before, after, and/or as part of the one or more cooling steps. For example, in embodiments wherein the pretreated biomass is separated into a solid fraction and a liquid fraction, where only the solid fraction is fed to enzymatic hydrolysis, the pH of the liquid fraction may require adjustment prior to being fed to fermentation (e.g., separate from, or with, the hydrolyzate from the solid fraction). For example, in one embodiment, the pH of the liquid fraction is adjusted to the pH optimum of the microorganism used in a subsequent fermentation step. For example, *Saccharomyces cerevisiae* may have optimum pH values between about 4 and about 5.5.

In one embodiment, enzyme is added to and/or mixed with the pretreated biomass (e.g., either the solid fraction or whole) prior to feeding the pretreated biomass to the hydrolysis reactor. In one embodiment, enzyme addition is after cooling and alkali addition.

As discussed above, the pretreated biomass may be washed. However, it can also be fed to enzymatic hydrolysis with minimal washing, or without washing. While washing may remove potential inhibitors and/or inactivators, and thus increase enzyme efficiency, it may also remove fermentable sugars, and thus reduce ethanol yield. Providing little or no washing of the pretreated biomass is advantageous in that it requires less process water and provides a simpler process.

Enzymatic Hydrolysis

The cellulose in the lignosulfonic acid pretreated biomass can be hydrolyzed to glucose after the addition of a suitable enzyme. In one embodiment, enzyme addition includes the addition of cellulase, which is an enzyme(s) that breaks cellulose chains into glucose. In particular, the term "cellulase" refers to any of several enzymes produced by fungi, bacteria, or protozoans that catalyze cellulolysis. For example, the term cellulase may denote a multi-enzyme mixture comprising exo-cellobiohydrolases (CBH), endo-glucanases (EG), and β-glucosidases (βG) that can be produced by a number of plants and microorganisms. Among the most widely studied, characterized and commercially produced cellulases are those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EGV and EGVI cellulases have been isolated from *Humicola insolens*. In addition to CBH, EG and βG, there are several accessory enzymes that may aid in the enzymatic digestion of cellulose, including glycoside hydrolase 61 (GH61), swollenin, expansin, lucinen and cellulose-induced protein (Cip). For example, in one embodiment the enzyme added contains GH61, which may improve hydrolysis. In one embodiment, the enzyme added comprises a commercial cellulase cocktail that is suitable for use in the methods/processes described herein.

In one embodiment, enzyme addition is achieved by adding enzyme to a reservoir, such as a tank, to form an enzyme solution, which is then introduced to the pretreated biomass. In one embodiment, enzyme is added to the washed solid fraction of the pretreated biomass. In one embodiment, enzyme is added to a pH adjusted slurry of pretreated biomass that includes both liquid and solid portions of the pretreated biomass.

In general, the enzyme dose may depend on the activity of the enzyme at the selected pH and temperature, the reaction time, the volume of the reactor, and/or other parameters. It should be appreciated that these parameters may be adjusted as desired by one of skill in the art. In one embodiment, cellulase is added at a dosage between about 2 to 20 mg protein per gram cellulase, between about 2 to 15 mg protein per gram cellulase, or between about 2 to 12 mg protein per gram cellulase. The protein may be quantified using either the bicinchoninic acid (BCA) assay or the Bradford assay. In one embodiment, the initial concentration of cellulose in the slurry, prior to the start of enzymatic hydrolysis, is between about 0.01% (w/w) to about 20% (w/w).

In one embodiment, the enzymatic hydrolysis is carried out at a pH and temperature that is at or near the optimum for the added enzyme. For example, in one embodiment, the enzymatic hydrolysis is carried out at one or more temperatures between about 30° C. to about 95° C., between about 50° C. to about 60° C., or between about 45° C. to about 55° C. In one embodiment, the enzymatic hydrolysis is carried such that the initial pH is, and/or such that the pH is maintained, between about 3.5 and about 8.0, between about 4 and about 6, or between about 4.8 and about 5.5.

In one embodiment, the enzymatic hydrolysis is carried out for a time period of about 10 to about 250 hours, or about 50 to about 250 hours. In one embodiment, the enzymatic hydrolysis is carried out for at least 24 hours, at least 36 hours, at least 48 hours, or at least 80 hours. In one embodiment, the enzymatic hydrolysis is carried out for at least 72 hours. In general, conducting the enzymatic hydrolysis for at least 24 hours will promote hydrolysis of both the amorphous and crystalline cellulose.

In general, the enzymatic hydrolysis may be conducted as a batch process, a continuous process, or a combination thereof. In addition, the enzymatic hydrolysis may be agitated, unmixed, or a combination thereof. In one embodiment, the enzymatic hydrolysis is conducted in one or more dedicated hydrolysis reactors, connected in series or parallel. In one embodiment, the one or more hydrolysis reactors are jacketed with steam, hot water, or other heat sources. In one embodiment, the enzymatic hydrolysis is conducted in one or more continuous stirred tank reactors (CSTRs) and/or one or more plug flow reactors (PFRs). In plug flow reactors, the slurry is pumped through a pipe or tube such that it exhibits a relatively uniform velocity profile across the diameter of the pipe/tube and such that residence time within the reactor provides the desired conversion. In one embodiment, the hydrolysis includes a plurality of hydrolysis rectors including a PFR and a CSTR in series. In one embodiment, the enzymatic hydrolysis and fermentation are conducted in separate vessels so that each biological reaction can occur at its respective optimal temperature. In one embodiment, the enzymatic hydrolysis and fermentation are conducted is a same vessel, or series of vessels.

In one embodiment, oxygen is added to one or more of the hydrolysis reactors. In one embodiment, the dissolved oxygen concentration within one or more hydrolysis reactors is maintained at a certain level. In one embodiment, the dissolved oxygen concentration is maintained within a range that is sufficient for the full activity of lytic polysaccharide monooxygenases (LPMOs) or any other oxygen-dependent components of the catalyst used to effect hydrolysis. In one embodiment, air or oxygen is bubbled into the slurry or headspace of one or more of the hydrolysis reactors.

In one embodiment, the hydrolyzate provided by enzymatic hydrolysis is filtered to remove insoluble lignin and/or undigested cellulose, and a portion thereof is used to cultivate additional enzyme for the enzymatic hydrolysis (e.g., fermentation with *Trichoderma* sp. or *Talaromyces* sp.), whereas the remaining glucose is fermented to an alcohol.

Fermentation

In one embodiment, the sugars produced during enzymatic hydrolysis and/or lignosulfonic acid pretreatment are fermented via one or more microorganisms to produce a fermentation product. In general, the fermentation microorganism(s) may include any suitable yeast and/or bacteria.

In one embodiment, hydrolyzate produced during enzymatic hydrolysis is subjected to a fermentation with *Saccharomyces* spp. yeast. For example, in one embodiment, the fermentation is carried out with *Saccharomyces cerevisiae*, which has the ability to utilize a wide range of hexoses such as glucose, fructose, sucrose, galactose, maltose, and maltotriose to produce a high yield of ethanol. In one embodiment, the glucose and/or other hexoses derived from the cellulose are fermented to ethanol using a wild-type *Saccharomyces cerevisiae* or a genetically modified yeast. In one embodiment, the fermentation is carried out with *Zymomonas mobilis* bacteria.

In one embodiment, hydrolyzate produced during enzymatic hydrolysis is fermented by one or more microorganisms to produce a fermentation broth containing butanol. For example, in one embodiment the glucose produced during enzymatic hydrolysis is fermented to butanol with *Clostridium acetobutylicum*.

In one embodiment, one or more of the pentoses produced during the pretreatment is fermented to ethanol via one or more organisms. For example, in one embodiment, xylose is fermented to butanol and/or ethanol by *Clostridia* bacteria. In one embodiment, the xylose and other pentose sugars produced during the pretreatment are fermented to xylitol by yeast strains selected from the group consisting of *Candida, Pichia, Pachysolen, Hansenula, Debaryomyces, Kluyveromyces* and *Saccharomyces*.

In general, the C6 sugar from the enzymatic hydrolysis and the C5 sugars from the liquid fraction of the pretreated biomass can be subjected to separate fermentations or a combined fermentation. For example, consider the case where the pretreated biomass is subject to a solid/liquid separation and only the solid fraction is fed to enzymatic hydrolysis. In this case, the glucose produced by enzymatic hydrolysis can be fermented on its own, or can be combined with the liquid fraction and then fermented. For example, in one embodiment, a sugar solution containing both the pentose and hexose sugars is fermented to ethanol using only *Saccharomyces cerevisiae*. In one embodiment, a sugar solution containing both pentose and hexose sugars is fermented to ethanol using a mixture wherein pentose utilizing and ethanol producing yeasts (e.g., such as *Pichia fermentans* and *Pichia stipitis*) are cocultured with *Saccharomyces cerevisiae*. In one embodiment, a sugar solution containing both pentose and hexose sugars is fermented using genetically engineered *Saccharomyces* yeast capable of cofermenting glucose and xylose.

In general, the dose of the microorganism(s) will depend on a number of factors, including the activity of the microorganism, the desired reaction time, the volume of the reactor, and/or other parameters. It should be appreciated that these parameters may be adjusted as desired by one of skill in the art to achieve optimal conditions. In one embodiment, the fermentation is supplemented with additional nutrients required for the growth of the fermentation microorganism. For example, yeast extract, specific amino acids, phosphate, nitrogen sources, salts, trace elements and vitamins may be added to the hydrolyzate slurry to support their growth. In one embodiment, yeast recycle is employed. In one embodiment, the fermentation is carried out at a pH and temperature that is at or near the optimum for the added microorganism. For example, *Saccharomyces cerevisiae* may have optimum pH values between about 4 and about 5.5 and a temperature optimum between about 25° C. and about 35° C. In one embodiment, the fermentation is carried out at one or more temperatures between about 25° C. to about 55° C. In one embodiment, the fermentation is carried out at one or more temperatures between about 30° C. to about 35° C.

In general, the fermentation may be conducted as a batch process, a continuous process, or a fed-batch mode. For example, in one embodiment, the fermentation is conducted in continuous mode, which may offer greater productivity and lower costs. In one embodiment, the enzymatic hydrolysis may be conducted in one or more fermentation tanks, which can be connected in series or parallel. In general, the fermentation may be agitated, unmixed, or a combination thereof. For example, in one embodiment, the fermentation is conducted one or more continuous stirred tank reactors (CSTRs) and/or one or more plug flow reactors (PFRs). In one embodiment, the one or more fermentation tanks are jacketed with steam, hot water, or other heat sources. In one embodiment, the enzymatic hydrolysis and fermentation are conducted in separate vessels so that each biological reaction can occur at its respective optimal temperature. In another embodiment, the hydrolysis (e.g., which may be also referred to as saccharification) is conducted simultaneously with the fermentation in same vessel. For example, in one embodiment, a simultaneous saccharification and fermentation (SSF) is conducted at temperature between about 35° C. and 38° C., which is a compromise between the 50° C. to 55° C. optimum for cellulase and the 25° C. to 35° C. optimum for yeast.

Alcohol Recovery

Any fermentation product (e.g., alcohol) produced during fermentation can be recovered, a process wherein the fermentation product is concentrated and/or purified from the fermented solution (e.g., which may or may not have been subjected to a solids-liquid separation to remove unconverted cellulose, insoluble lignin, and/or other undissolved substances). In one embodiment, alcohol recovery uses one or more distillation columns that separate the alcohol from other components (e.g., water). In general, the distillation column(s) in the distillation unit may be operated in continuous or batch mode, although are typically operated in a continuous mode. Heat for the distillation process may be introduced at one or more points, either by direct steam injection or indirectly via heat exchangers. When the alcohol is ethanol, after distillation, the water remaining in the concentrated ethanol stream (i.e., vapour) may be removed from the ethanol rich vapour by a molecular sieve resin, by membrane extraction, or other methods known to those of skill in the art for concentration of ethanol beyond the 95% that is typically achieved by distillation (e.g., a vapour phase drying). The vapour may then be condensed and denatured.

Acid and/or Lignosulfonate Recovery

In one embodiment, lignosulfonic acid generated during and/or provided for the pretreatment is recovered following pretreatment, enzymatic hydrolysis, and/or fermentation. In one embodiment, lignosulfonate generated during and/or provided for the pretreatment is recovered following pretreatment, enzymatic hydrolysis, and/or fermentation.

The lignosulfonic acid and/or lignosulfonate may be recovered for energy production (e.g., combusted) or for producing value-added materials. For example, lignosulfonates have been used as a dispersing agent (e.g., in textile dyes, cement admixtures, or fertilizers), a binding agent (e.g., in carbon black, ceramics, plasterboard, or animal feed), a surfactant (e.g., in detergents, leather tanning, or pesticides), an additive in oil and gas drilling, an emulsion stabilizer, an extrusion aid, in the production of vanillin, and in dust control applications.

The lignosulfonic acid and/or lignosulfonate may be recovered by any method used to produce lignosulfonate products (e.g., provided in liquid form or as a powder). For example, the lignosulfonic acid and/or lignosulfonate may be recovered using a method conventionally used for recovering lignosulfonates from waste liquor (e.g., brown or red) of sulfite pulping process.

In general, the recovery method may be dependent on the desired product. For example, in some cases, it is acceptable for a lignosulfonate product to contain a relatively large amount of pentoses and/or other impurities so that the recovery may simply consist of concentrating and/or drying a liquid stream containing the lignosulfonate. In other cases, it is preferable to remove at least some of the impurities (e.g., which may be processed separately) and/or otherwise isolate at least a portion of the lignosulfonate. For example, lignosulfonate recovery may be achieved by precipitation and subsequent filtering, membrane separation, amine extraction, ion exchange, dialysis, or any combination thereof. The at least partially purified lignosulfonate may be concentrated (e.g., using an evaporator or membrane) and/or is optionally dried (e.g., using a vacuum dryer, drum dryer, etc.).

In one embodiment, the lignosulfonate is recovered by precipitation followed by separation of the liquid and precipitate. For example, precipitation may be induced by adding a precipitation agent and/or adjusting the pH. In general, lignosulfonate is soluble in water over a wide pH range and thus is not always readily isolated by pH modification alone. However, when a relatively large amount of calcium ions is added (e.g., via addition of an excess of lime), calcium lignosulfonate may precipitate out at high pH values (e.g., above about 12). This process, which may be generally known as the Howard process, may be more effective when the lignosulfonate has a relatively high molecular weight. In other embodiments, a precipitating agent other than lime is used. For example, lignosulfonate may be precipitated as a barium salt.

In one embodiment, the lignosulfonate is recovered using membrane separation. For example, in one embodiment, the lignosulfonate is recovered using ultrafiltration. Ultrafiltration is advantageous in that high-molar mass lignosulfonates can be separated from the low molar mass carbohydrates such as xylose, thereby also providing the means to simultaneously recovery xylose and lignosulfonate. In one embodiment, the lignosulfonate is recovered from a series of membranes, wherein the cut-off for a second membrane is lower than the cut-off for the first membrane.

In one embodiment, the lignosulfonate is recovered using amine extraction. For example, in one embodiment the lignosulfonate is recovered by contacting an aqueous solution containing lignosulfonic acid with one or more amines (e.g., a long chain aliphatic amine or a tertiary amine) dissolved in an essentially water insoluble alcohol (i.e., an aliphatic alcohol) or other diluent. This results in the formation of an amine-lignosulfonic acid complex which is soluble in the alcohol but insoluble in the aqueous solution. More specifically, it results in the formation of two liquid phases that can be separated, the first an alcohol-organic phase that contains the amine complex, and the second an aqueous-organic phase that may contain some lignosulfonate and/or carbohydrates (e.g., pentoses). In one embodiment, the ratio of amine to alcohol is between 3:7 and 6:4, by volume. For example, in one embodiment, the lignosulfonate is recovered by contacting a solution containing lignosulfonic acid with amaline-nonylphenol (A-NP), which is a mixture of tri-n-octylamine, tri-n-decylamine, and nonylphenol (15:15:70, by volume). In one embodiment, the lignosulfonate is recovered by contacting a solution containing lignosulfonic acid with a mixture of tri-n-octylamine, tri-n-decylamine, and 1-octanol (9:9:82, by volume). Lignosulfonate may be recovered from the amine-complex containing phase by any suitable method. For example, in one embodiment, lignosulfonate is separated from the organic phase by treatment with a stripping agent. In one embodiment, lignosulfonate is separated from the organic phase by back extraction with a strong base such as NaOH.

In one embodiment, the lignosulfonate is recovered by contacting an aqueous solution of lignosulfonic acid with an ion exchange resin. In general, any suitable ion exchange technology or combination of ion exchange technologies may be used. For example, a chromatographic column packed with a strongly acidic resin in metal salt form has been reportedly used to fractionate sulfite spent liquor into a lignosulfonate rich fraction and a sugar rich fraction, and may be suitable for the processes described herein. In this case, the feed was at a pH of 2.5-3.5, and the resin was a sulfonated polystyrene divinylbenzene, where the metal salt corresponded to the pulping cation. Alternatively, a non-ionic resin may be suitable for recovering lignosulfonates in various embodiments the instant invention. For example, it has been reported that Amberlite XAD-7 HP, which is a poly(methyl methacrylate) resin, may be used for the quantitative isolation of lignosulfonates from spent sulfite liquors. The lignosulfonates were eluted with ethanol. In this case, the adsorption of lignosulfonate on the column was found to be dependent on the pH of the solution, and as a result, the spent sulfite liquor was first contacted with a strong cation exchange resin in order to lower the pH. Further alternatively, an anion exchange resin may be suitable for recovering lignosulfonates in various embodiments the instant invention. For example, in one embodiment, a weak base resin is used. Weak base resins, which are capable of sorbing strong acids with a high capacity and are readily regenerated with caustic, have been studied for simultaneously separating xylo-oligosaccharides and lignosulfonate from wheat straw magnesium bisulfite pretreatment spent liquor, and appear to have potential. Advantageously, ion exchange chromatography can be used at the industrial level.

Advantageously, at least partially purifying the lignosulfonate using one of these methods allows lignosulfonate to be processed separately from the carbohydrates (e.g., xylose). For example, xylose may be fermented to increase the yield of ethanol in an ethanol production process, or may be converted to a value-added product (e.g., xylitol, biogas, etc.). The lignosulfonate may be used to produce a different value-added product (e.g., vanillin, dispersant, binder, cement or food additive, etc.). In one embodiment, the lignosulfonate is recycled within the process. For example, in one embodiment, at least a portion of the recovered lignosulfonate is reintroduced into a pretreatment reactor. In some cases, the recovered lignosulfonate will be first contacted with a cation exchange resin, which protonates some of the sulfonate groups.

Advantageously, recovering lignosulfonic acid and/or lignosulfonate from the pretreatment process described herein may be advantageous over recovering lignosulfonate from a sulfite pulping process. In sulfite pulping processes, lignosulfonates are generally recovered, sold, and/or shipped as salts. In these cases, the salt may depend on the counter ion used in the sulfite pulping process (e.g., may be determined by the sulfite salt, or base, used), and/or may be determined by the lignosulfonate recovery method. For example, the most common recovery process may be the Howard method, wherein calcium lignosulfonate is precipitated from the spent liquor of a calcium sulfite pulping process via the addition of excess lime. In this case, if a different salt is desired, one or more additional steps must be taken to exchange the counter ions.

When pretreating with a relatively high concentration of lignosulfonic acid, in the absence of a large concentration of pulping cation, a significant number of the sulfonate groups on the lignin may be in acid form. This acid functionality may facilitate and/or simplify the recovery process. For example, since a significant number of the sulfonate groups on the lignin may be in acid form, a desired counter ion may be introduced, while obviating the extra steps to exchange counter ions (e.g., a calcium lignosulfonate intermediate can be obviated). This may increase the commercial value of lignosulfonate product and/or decrease production costs.

Moreover, since a significant number of sulfonate functional groups are in the acid form, the functionality of these groups can facilitate at least partial purification/recovery of the lignosulfonate. For example, lignosulfonic acid may be extracted directly with amines or by using ion exchange (e.g., adsorbed on an anion exchange resin), without having to first strip off the cations. Accordingly, the process and system described herein can provide a biorefinery that generates both ethanol and value-added lignin products, thus increasing the yield of marketable products from the lignocellulosic biomass. In particular, it allows the value of each stream to be maximized and the opportunity to generate additional fuels or chemicals (e.g., bioproducts).

In general, when sulfur dioxide is used in the lignosulfonic acid pretreatment, excess sulfur dioxide not consumed during the pretreatment can be recovered and/or recycled. For example, in one embodiment, the pretreated biomass is flashed, and the flash stream, which contains excess sulfur dioxide, is fed to a sulfur dioxide recovery unit. In general, any suitable sulfur dioxide technology may be used, and may for example, use a condenser, a sulfur dioxide stripper, a sulfur dioxide scrubbing system, a regenerative sulfur dioxide scrubbing system, a sulfur burner, etc. In one embodiment, the recovered sulfur dioxide, which is optionally stored temporarily, is recycled directly back into the process. In one embodiment, the recycling includes generating gaseous sulfur dioxide from liquid sulfur dioxide for impregnating the lignocellulosic biomass, or forming a sulfurous acid solution that is used to impregnate the lignocellulosic biomass. In one embodiment, gaseous sulfur dioxide is compressed and stored for recycling back into the process. Advantageously, sulfur dioxide recovery allows the recycling of sulfur within the system, and thus improves the process economics (e.g., since less sulfur dioxide and/or sulfurous acid needs to be purchased for pretreatment). In addition, sulfur dioxide recovery improves the economics of using a high sulfur dioxide loading, particularly, when the sulfur dioxide recovery is efficient at high sulfur dioxide concentrations.

Advantageously, since the pretreatment is conducted in the presence of lignosulfonic acid, to which counter cations have a strong affinity, most of the added $SO_2$ will be in acid form (i.e., uncombined $SO_2$), thus facilitating $SO_2$ recovery by flashing. Since the recovery may be relatively simple and efficient, the cost of the relatively high sulfur loading is not as limiting. Further advantageously, since the pretreatment is conducted in the presence of lignosulfonic acid, wherein the fraction of sulfonate groups in acid form is relatively high, the recovery of lignosulfonate may be achieved using a recovery technology that is more effective when the lignosulfonic acid is in acid form (e.g., amine extraction), without requiring a preliminary strong cation exchange.

To facilitate a better understanding of embodiments of the instant invention, the following examples of certain aspects of some embodiments are given. In no way should the following examples be read to limit, or define, the entire scope of the invention.

EXAMPLES

Example 1: Preparation of Lignosulfonic Acid

Lignosulfonic acid was prepared by dissolving about 33 g of commercial sodium lignosulfonate (Pfaltz and Bauer Inc, CAS 8061-51-6) in 100 mL of deionized water. The resulting solution was passed over a column, which was packed with a strong cation exchange resin in the $H^+$ form, several times. Before use, the cation exchange resin (i.e., Purolite C-150S C, which has a macroporous, styrene-divinylbenzene polymer support) was activated with 0.4M sulfuric acid, and then washed with deionized water. The pH of the lignosulfonic acid collected from the column was 0.51. The concentration of lignosulfonic acid in this solution has been calculated to be 0.3 mol/L.

Example 2: Pretreatment with Lignosulfonic Acid

Wheat straw was hammer-milled such that a large portion of the particles was less than about 1 inch (2.54 cm) length and ¼ inch (0.635 cm) width. In general, less than 5% of the particles were longer than 2 inches (5.08 cm) and up to 10% of the particles were fines, the size of dust. The glucan content of the straw was 34.18%, the xylan content was 19.88%, and the lignin content was 23.38% on a dry basis. The total solids (TS) content of the straw was 92.61%. The carbohydrate assay was based on Determination of Structural Carbohydrates and Lignin in Biomass-LAP (Technical Report NREL/TP-510-42618).

Solutions of $H_2SO_3$ and lignosulfonic acid were prepared using sulfurous acid solution (≥6% $H_2SO_3$, from Sigma-Aldrich) and the lignosulfonic acid solution (i.e., prepared according to Example 1), in 35 mL bottles. Lignocellulosic slurries were prepared by adding the $H_2SO_3$/lignosulfonic acid solutions to the wheat straw, with a target consistency of about 10%. The slurries were prepared in 25 mL stainless steel, laboratory tubular reactors (i.e., about 5 inches in length). Once the solutions were added to the wheat straw, the reactors were sealed. The slurries were prepared in duplicate, with one opened after a ten minute soak and used for measuring the initial pH, while the other remained sealed. The sealed reactors were placed within the oil bath within 15 minutes. Each sealed reactor was heated at 130° C. for a predetermined time (e.g., 15, 30, 60, 90 minutes). At the end of the heating period, each reactor was cooled in an ice bath. Experiments conducted with $SO_2$ were carried out in a fume hood. The details for each run are outlined in Table 1.

TABLE 1

Pretreatment conditions for various lignosulfonic acid pretreatments

| Run | Approx dry biomass (g) | Volume of 7.05% w/w of $H_2SO_3$ (mL) | Volume of lignosulfonic acid at pH 0.51 (mL) | Volume of water (mL) | Initial pH | Final pH (at 120 mins) |
|---|---|---|---|---|---|---|
| 1 | 1.55 | 7.38 | — | 5.62 | 1.21 | 1.03 |
| 2 | 1.51 | 7.38 | 4.91 | 0.71 | 0.8 | 0.68 |
| 3 | 1.51 | 7.38 | 2.82 | 2.80 | 0.9 | 0.80 |
| 4 | 1.51 | 7.38 | 1.25 | 4.37 | 1.0 | 0.90 |

As evident from Table 1, the initial pH for each run where lignosulfonic acid was added (i.e., Runs 2-4) was well below the initial pH of the run utilizing only $SO_2$ (i.e., Run 1), even though the same total amount of $SO_2$ was added. The total amount of $SO_2$ added and the concentration of lignosulfonic acid (LSA) for each of these runs is summarized in Table. 2.

TABLE 2

Calculated concentrations for the various lignosulfonic acid pretreatments

| Run | Total amount of $SO_2$ (wt % on dry solids) | Total amount of $H_2SO_3$ (wt % on dry solids) | Initial Conc. of $H_2SO_3$ (mol/L) | Initial Conc. of LSA (mol/L) | Conc. of LSA formed in situ (mol/L) | Conc. of LSA-added and formed in situ (mol/L) |
|---|---|---|---|---|---|---|
| 1 | 26.2 | 33.6 | 0.488 | 0 | 0.063 | 0.063 |
| 2 | 26.9 | 34.5 | 0.488 | 0.117 | 0.062 | 0.179 |
| 3 | 26.9 | 34.5 | 0.488 | 0.067 | 0.044 | 0.111 |
| 4 | 26.9 | 34.5 | 0.488 | 0.030 | 0.039 | 0.069 |

The concentration of LSA formed in situ is calculated based on the change in pH (e.g., initial versus final in Table 1). Referring to Table 2, the data indicates that the concentration of LSA added and formed in situ may increase as the amount of lignosulfonic acid added is increased.

Example 3: Analysis of Pretreated Material

A portion of the pretreated material was reserved for analysis. The undissolved solids (UDS) concentration, total solids (TS) concentration, dissolved solids (DS) concentration, were determined calculated according the methodology set out in Examples 3, 4, and 5 of U.S. Pat. No. 9,574,212, which is hereby incorporated by reference and particularly for the purpose of describing such methodology.

The concentration of monomeric sugars (e.g., concentration of glucose and/or xylose) in the pretreated material was determined using high performance liquid chromatography (HPLC). More specifically, the concentration of monomeric sugars such as xylose was calculated according the methodology set out in Example 6 of U.S. Pat. No. 9,574,212, which is hereby incorporated by reference and particularly for the purpose of describing such methodology.

The carbohydrate content of the pretreated material was ascertained with a carbohydrate assay based on Determination of Structural Carbohydrates and Lignin in Biomass-LAP (Technical Report NREL/TP-510-42618). This assay can provide the cellulose content, xylan content, insoluble lignin content, and lignin content of the pretreated biomass, w/w on a dry basis. For example, the cellulose/glucan content, xylan content, and/or lignin content was determined using the methodology set out in Example 11 of U.S. Pat. No. 9,574,212, which is hereby incorporated by reference and particularly for the purpose of describing such methodology.

Figure 8:
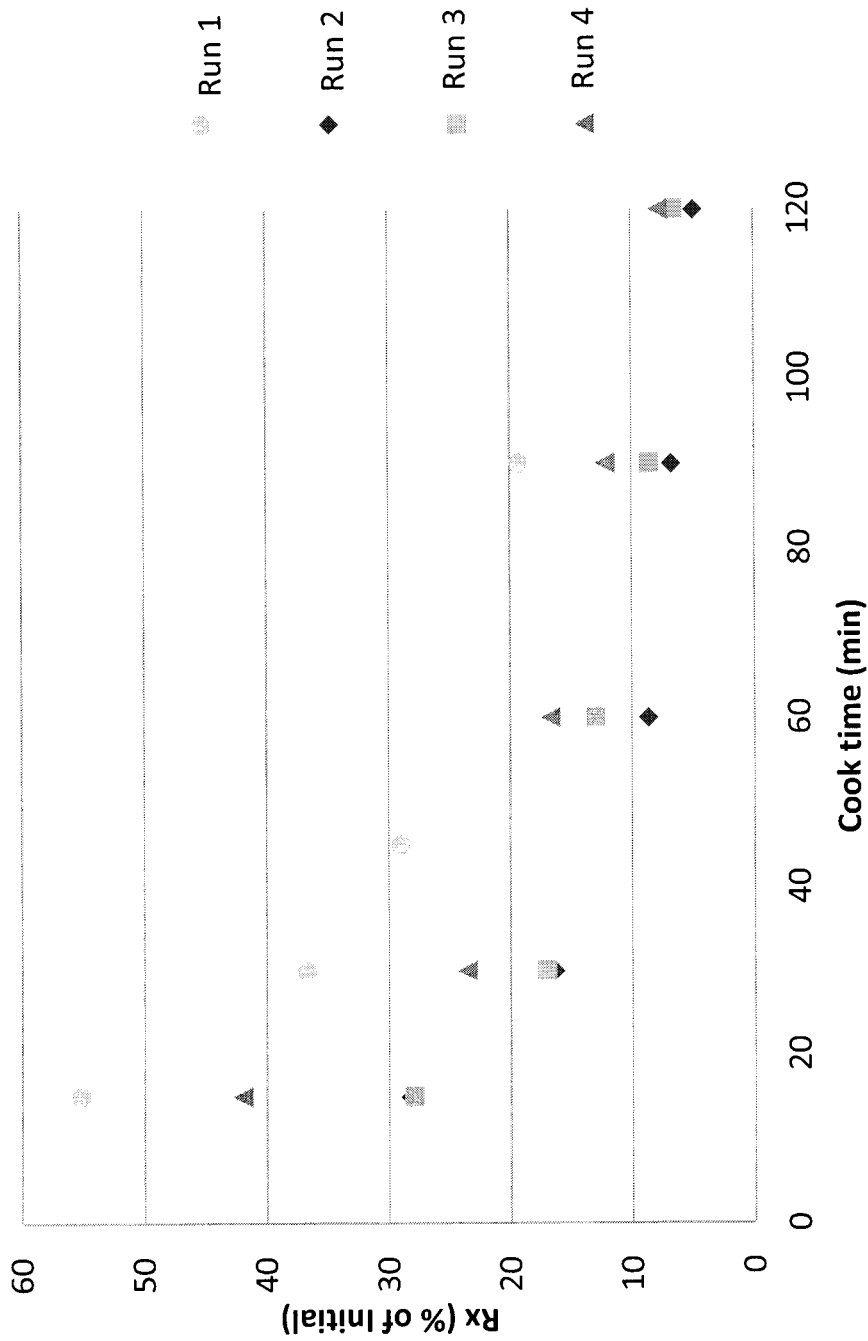
FIG. 8 is a plot of residual xylan versus cook time for various pretreatments with lignosulfonic acid.

A plot of residual xylan versus cook time for Runs 1-4 is provided in FIG. 8. Referring to FIG. 8, the addition of lignosulfonic acid results in the residual xylan level ($R_x$) dropping significantly (i.e., eventually down to about 5 wt %). Accordingly, the data indicates that the presence of lignosulfonic acid in pretreatment significantly contributes to the dissolution of hemicellulose, and that increasing and/or optimizing the concentration of lignosulfonic acid (e.g., added or generated in situ) may further increase hemicellulose dissolution.

The residual xylan, xylose yield, lignin dissolution, and furfural yield, for Runs 1-4, as measured for the 120 minute cook, are summarized in Table 3.

does not appear to degrade xylose to the same extent that HCl or $H_2SO_4$ does (i.e., at the same pH). Moreover, these results appear to indicate that the lignosulfonic acid may have a protective effect with regard to the xylose.

Figure 9:
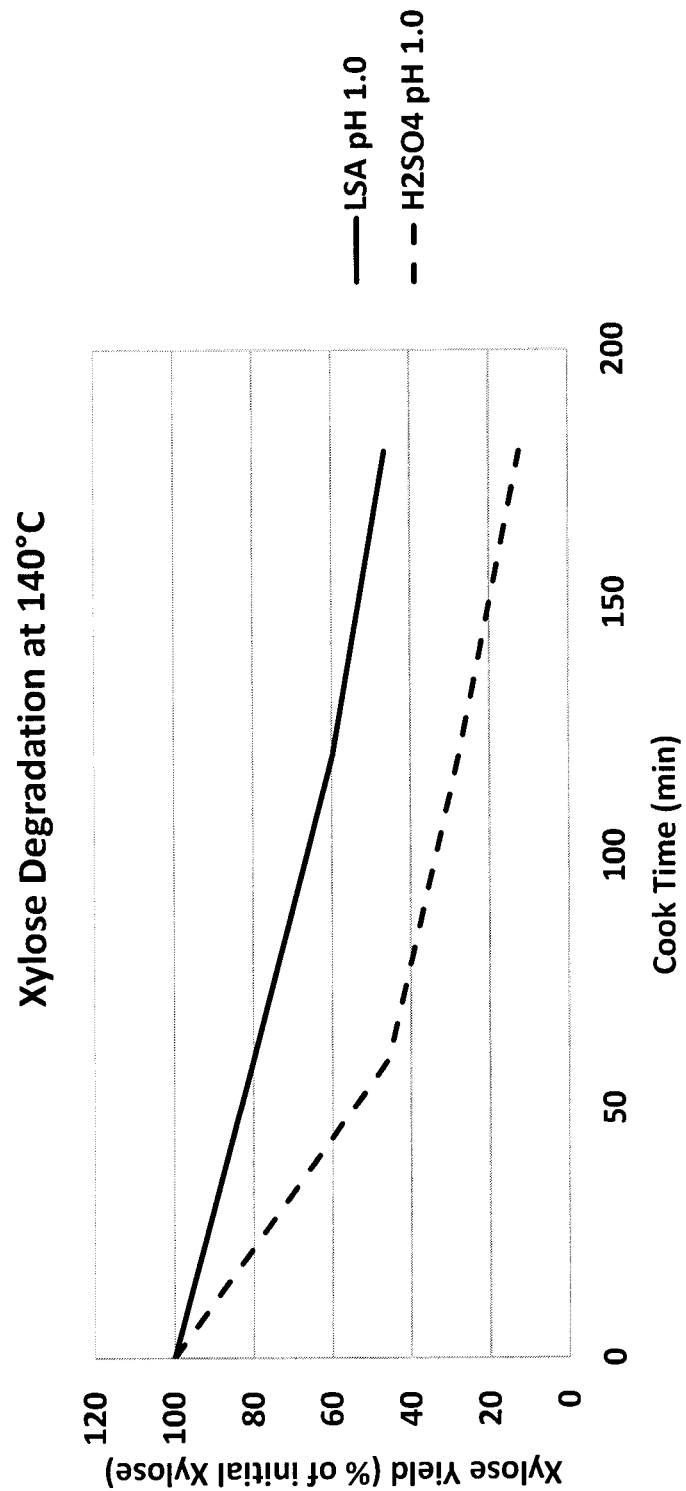
FIG. 9 is a plot of xylose (as a percent of xylose initially present) versus cook time, when xylose is heated with lignosulfonic acid or sulfuric acid.

FIG. 9 is a plot of xylose concentration (as a percent of xylose initially present) versus cook time, when xylose is heated with LSA or sulfuric acid. For these experiments, laboratory tubular reactors were charged with stock xylose solution (50 g/L), water, and stock acid solution in amounts selected to provide an initial xylose concentration of about 20 g/L and a pH of 1. Xylose was obtained from Sigma-Aldrich. For the LSA experiment, the stock acid solution was prepared according to Example 1 (e.g., pH~0.5). For the sulfuric acid experiment, the stock acid solution was 72 wt % $H_2SO_4$. The mixtures were heated at 140° C. Referring to FIG. 9, after about 180 minutes, LSA only degraded about 54% of the xylose, whereas sulfuric acid degraded about 88% of the xylose, even though the pH was the same. Referring again to Table 3, the amount of lignin solubilized in each of Runs 1, 2, 3, and 4 was found to be 49.89%, 39.26%, 43.20%, and 55.17% (i.e., calculated from the amount of undissolved lignin remaining following pretreatment). While lignin dissolution generally decreased as the pH was lowered (e.g., by increasing the concentration of

TABLE 3

Analysis of pretreated materials following a 120 minute pretreatment

| Run | Total amount of $SO_2$ (wt % on dry solids) | Initial Conc. of LSA (mol/L) | Residual Xylan (% initial) | Xylose Yield (mole/mole anhydroxylan (%)) | Lignin dissolution (% of initial) | Furfural yield (mole/mole anhydroxylan (%)) |
|---|---|---|---|---|---|---|
| 1 | 26.2 | 0 | 16.24 | 83.16 | 49.89 | 0 |
| 2 | 26.9 | 0.117 | 9.46 | 82.78 | 39.26 | 0.7 |
| 3 | 26.9 | 0.067 | 10.60 | 86.02 | 43.20 | 0.37 |
| 4 | 26.9 | 0.030 | 4.92 | 85.48 | 55.17 | 0.26 |

Referring to Table 3, the addition of lignosulfonic acid resulted in the residual xylan level ($R_x$) dropping from 16.24% to 4.92%. Advantageously, this significant increase in hemicellulose dissolution is achieved simply by adding lignosulfonic acid, which can be a by-product of $SO_2$ pretreatment, and moreover, is achieved with the same amount of $SO_2$. Since lignosulfonic acid can be a by-production of this pretreatment, its addition does not introduce any new chemicals to the pretreatment and/or significantly complicate chemical recovery. Further advantageously, this increase in hemicellulose dissolution is not necessarily accompanied by a decrease in xylose yield.

Conventionally, when residual xylan levels are driven down below 10% by the addition of a strong acid (e.g., HCl or $H_2SO_4$) or by increasing the reaction temperature above 160° C., the pentose sugars tend to degrade, and xylose yields are reduced. However, in Runs 1, 2, 3, and 4, the xylose yields were found to be 83.16%, 82.78%, 86.02%, and 85.48%, respectively. In other words, even though the residual xylan level dropped from 16.24% to 4.92% (i.e., relative to initial xylan), the xylose yield did not drop significantly. Moreover, some of the highest xylose yields achieved were when lignosulfonic acid was added. Accordingly, the data indicates that although lignosulfonic acid is a strong acid and can promote hemicellulose dissolution, it lignosulfonic acid added), adding a relatively small amount of lignosulfonic acid yielded the highest lignin dissolution. In fact, Run 4, which corresponds to adding lignosulfonic acid to pretreatment such that the initial lignosulfonic acid concentration was about 0.030 mol/L yielded one of the highest xylose yields and the highest lignin dissolution.

Of course, the above embodiments have been provided as examples only. It will be appreciated by those of ordinary skill in the art that various modifications, alternate configurations, and/or equivalents will be employed without departing from the spirit and scope of the invention. For example, although it has been found that subjecting lignocellulosic biomass to a lignosulfonic acid pretreatment wherein a total amount of sulfur dioxide is greater than 15 wt % and wherein the concentration of lignosulfonic acid is greater than 0.02 mol/L has its advantages, adding lignosulfonic acid to any type of pretreatment may be advantageous. In one embodiment, lignosulfonic acid is added to a sulfite pretreatment, an acid sulfite pretreatment, a bisulfite pretreatment, or an organosolv-type pretreatment (e.g., to provide concentration of lignosulfonic acid that is greater than 0.02 mol/L). Accordingly, the scope of the invention is therefore intended to be limited solely by the scope of the appended claims.

The invention claimed is:

1. A process for converting lignocellulosic biomass to a fermentation product, said process comprising:
providing the lignocellulosic biomass;
subjecting the lignocellulosic biomass to a lignosulfonic acid pretreatment wherein the concentration of lignosulfonic acid is greater than 0.02 mol/L and wherein a total amount of sulfur dioxide is greater than 15 wt % based on dry weight of lignocellulosic biomass, said lignosulfonic acid pretreatment conducted between 110° C. and 150° C. for at least 30 minutes, thereby providing a pretreated slurry comprising cellulose;
subjecting at least the cellulose to an enzymatic hydrolysis to provide glucose;
subjecting at least the glucose to a microbial fermentation to produce the fermentation product; and,
recovering the fermentation product,
wherein at least a portion of the lignosulfonic acid is added to the pretreatment.

2. The process according to claim 1, comprising separating the pretreated slurry into a liquid stream and a solids stream, wherein the solids stream comprises the cellulose and the liquid stream comprises xylose and lignosulfonate.

3. The process according to claim 2, comprising washing solids in the solids stream, and wherein subjecting at least the cellulose to an enzymatic hydrolysis comprises mixing the washed solids with cellulase and maintaining the mixture at a temperature and for a time effective to convert at least 60% of the cellulose in the lignocellulosic biomass to glucose.

4. The process according to claim 1, wherein subjecting at least the cellulose to an enzymatic hydrolysis comprises mixing a stream comprising the cellulose with cellulase and maintaining the mixture at a temperature and for a time effective to convert at least 60% of the cellulose to glucose.

5. The process according to claim 2, wherein subjecting the lignocellulosic biomass to a lignosulfonic acid pretreatment comprises adding the lignocellulosic biomass, sulfur dioxide, and lignosulfonic acid to a pretreatment reactor, and wherein the lignosulfonic acid added to the pretreatment reactor is derived from said process.

6. A process for converting lignocellulosic biomass to a fermentation product, said process comprising:
providing the lignocellulosic biomass;
subjecting the lignocellulosic biomass to a lignosulfonic acid pretreatment wherein the concentration of lignosulfonic acid is greater than 0.02 mol/L and wherein a total amount of sulfur dioxide is greater than 15 wt % based on dry weight of lignocellulosic biomass, said lignosulfonic acid pretreatment conducted between 110° C. and 150° C. for at least 30 minutes, thereby providing a pretreated slurry comprising cellulose;
subjecting at least the cellulose to an enzymatic hydrolysis to provide glucose;
subjecting at least the glucose to a microbial fermentation to produce the fermentation product; and,
recovering the fermentation product,
wherein the process comprises separating the pretreated slurry into a liquid stream and a solids stream, wherein the solids stream comprises the cellulose and the liquid stream comprises xylose and lignosulfonate, and
wherein the process comprises subjecting said liquid stream to at least one of a precipitation reaction and an ultrafiltration to provide lignosulfonic acid, and adding the lignosulfonic acid to the pretreatment reactor.

7. A process for converting lignocellulosic biomass to a fermentation product, said process comprising:
providing the lignocellulosic biomass;
subjecting the lignocellulosic biomass to a lignosulfonic acid pretreatment wherein the concentration of lignosulfonic acid is greater than 0.02 mol/L and wherein a total amount of sulfur dioxide is greater than 15 wt % based on dry weight of lignocellulosic biomass, said lignosulfonic acid pretreatment conducted between 110° C. and 150° C. for at least 30 minutes, thereby providing a pretreated slurry comprising cellulose;
subjecting at least the cellulose to an enzymatic hydrolysis to provide glucose;
subjecting at least the glucose to a microbial fermentation to produce the fermentation product; and,
recovering the fermentation product,
wherein the process comprises separating the pretreated slurry into a liquid stream and a solids stream, wherein the solids stream comprises the cellulose and the liquid stream comprises xylose and lignosulfonate, and
wherein the process comprises subjecting said liquid stream to at least one of an amine extraction and an ion exchange to provide lignosulfonic acid, and adding the lignosulfonic acid to the pretreatment reactor.

8. The process according to claim 7, wherein said at least one of an amine extraction and an ion exchange produces a lignosulfonate stream and a sugar stream, said sugar stream comprising xylose, and wherein said process further comprises subjecting said xylose to a fermentation reaction to produce the fermentation product.

9. The process according to claim 8, comprising recovering lignosulfonate from said lignosulfonate stream.

10. The process according to claim 1, wherein the total amount of sulfur dioxide is greater than 20 wt % based on dry weight of lignocellulosic biomass.

11. The process according to claim 1, wherein the total amount of sulfur dioxide is greater than 25 wt % based on dry weight of lignocellulosic biomass.

12. The process according to claim 1, wherein the total amount of sulfur dioxide is greater than 35 wt % based on dry weight of lignocellulosic biomass.

13. The process according to claim 1, wherein the total amount of sulfur dioxide is greater than 50 wt % based on dry weight of lignocellulosic biomass.

14. The method according to claim 1, wherein the lignocellulosic biomass comprises at least one of wheat straw and sugar cane bagasse.

15. The process according to claim 1, wherein at least one of the sulfur dioxide and lignosulfonic acid is added in an amount effective to provide an initial pH less than 1.1.

16. The process according to claim 1, wherein subjecting the lignocellulosic biomass to a lignosulfonic acid pretreatment comprises adding lignosulfonic acid having a pH less than 1 to a pretreatment reactor.

17. The process according to claim 1, wherein subjecting the lignocellulosic biomass to a lignosulfonic acid pretreatment comprises adding lignosulfonic acid having a pH less than 0.8 to a pretreatment reactor.

18. A process for converting lignocellulosic biomass to a fermentation product, said process comprising:
providing the lignocellulosic biomass;
subjecting the lignocellulosic biomass to a lignosulfonic acid pretreatment wherein the concentration of lignosulfonic acid is greater than 0.02 mol/L and wherein a total amount of sulfur dioxide is greater than 15 wt % based on dry weight of lignocellulosic biomass, said lignosulfonic acid pretreatment conducted between 110° C. and 150° C. for at least 30 minutes, thereby providing a pretreated slurry comprising cellulose;

subjecting at least the cellulose to an enzymatic hydrolysis to provide glucose;

subjecting at least the glucose to a microbial fermentation to produce the fermentation product; and, recovering the fermentation product, wherein the process comprises separating the pretreated slurry into a liquid stream and a solids stream, wherein the solids stream comprises the cellulose and the liquid stream comprises xylose and lignosulfonate, and wherein the process comprises contacting a stream comprising lignosulfonate with a cation exchange resin to provide an aqueous stream of lignosulfonic acid, and using at least a portion of the aqueous lignosulfonic acid stream in the lignosulfonic acid pretreatment.

19. The method according to claim 1, wherein the fermentation product is ethanol.

20. A process for converting lignocellulosic biomass to a fermentation product, said process comprising:

providing the lignocellulosic biomass;

subjecting the lignocellulosic biomass to a lignosulfonic acid pretreatment wherein the concentration of lignosulfonic acid is greater than 0.02 mol/L, said pretreatment conducted for at least 30 minutes, thereby providing a pretreated slurry comprising cellulose;

separating the pretreated slurry into a liquid stream and a solids stream, wherein the solids stream comprises cellulose and the liquid stream comprises xylose and lignosulfonate;

feeding lignosulfonic acid obtained or derived from said liquid stream to the pretreatment reactor;

subjecting the solids stream to an enzymatic hydrolysis that converts at least 60% of the cellulose in the lignocellulosic biomass to glucose;

subjecting at least the glucose to a microbial fermentation to produce the fermentation product;

recovering the fermentation product.

* * * * *

UNITED STATES PATENT AND TRADEMARK OFFICE
CERTIFICATE OF CORRECTION

PATENT NO. : 11,312,977 B2
APPLICATION NO. : 17/040738
DATED : April 26, 2022
INVENTOR(S) : Tolan et al.

It is certified that error appears in the above-identified patent and that said Letters Patent is hereby corrected as shown below:

On the Title Page

Page 4, Column 1 (item (56) Other Publications), Line 9, delete "Bioresour" and insert -- Bioresource --.

Page 4, Column 1 (item (56) Other Publications), Line 23, delete "Bioresouces," and insert -- Bioresources, --.

Page 4, Column 2 (item (56) Other Publications), Line 40, delete "Celluloytic" and insert -- Cellulolytic --.

In the Specification

Column 20, Line 10-13 (approx.), delete "$\dfrac{\dfrac{6\,g}{100\,g} * \dfrac{Mw\,SO_2}{Mw\,H_2SO_3}}{g\ biomass\ added - TS\ content} =$" and insert -- $\dfrac{\dfrac{6\,g}{100\,g} * \dfrac{Mw\,SO_2}{Mw\,H_2SO_3}}{g\ biomass\ added * TS\ content} =$ --.

Column 24, Line 52, delete "Myceliopthora," and insert -- Myceliophthora, --.

In the Claims

Column 36, Line 45, Claim 14, delete "method" and insert -- process --.

Column 37, Line 19, Claim 19, delete "method" and insert -- process --.

Signed and Sealed this
Twenty-third Day of August, 2022

Katherine Kelly Vidal
*Director of the United States Patent and Trademark Office*